US010188101B2

(12) United States Patent
Kamei et al.

(10) Patent No.: US 10,188,101 B2
(45) Date of Patent: Jan. 29, 2019

(54) METHOD FOR PRODUCING AN AGRICULTURAL PRODUCT

(75) Inventors: Masatoshi Kamei, Wakayama (JP); Hiromoto Mizushima, Wakayama (JP)

(73) Assignee: KAO CORPORATION, Tokyo (JP)

( * ) Notice: Subject to any disclaimer, the term of this patent is extended or adjusted under 35 U.S.C. 154(b) by 274 days.

(21) Appl. No.: 13/820,352

(22) PCT Filed: Sep. 1, 2011

(86) PCT No.: PCT/JP2011/069863
§ 371 (c)(1),
(2), (4) Date: Mar. 22, 2013

(87) PCT Pub. No.: WO2012/029893
PCT Pub. Date: Mar. 8, 2012

(65) Prior Publication Data
US 2013/0196854 A1    Aug. 1, 2013

(30) Foreign Application Priority Data

Sep. 3, 2010 (JP) ................. 2010-197725
Mar. 4, 2011 (JP) ................. 2011-047410
Mar. 4, 2011 (JP) ................. 2011-047411

(51) Int. Cl.
    *A01N 25/30*    (2006.01)
(52) U.S. Cl.
    CPC ................. *A01N 25/30* (2013.01)
(58) Field of Classification Search
    CPC ........ A01N 25/30; A01N 47/38; A01N 57/14; A01N 57/20
    USPC ......................... 504/358; 514/772
    See application file for complete search history.

(56) References Cited

U.S. PATENT DOCUMENTS

| 4,840,942 | A | 6/1989 | Iwasaki et al. |
| 5,668,086 | A | 9/1997 | Tadayuki et al. |
| 6,117,820 | A | 9/2000 | Cutler et al. |
| 2004/0053788 | A1 | 3/2004 | Hayashi et al. |
| 2004/0151749 | A1 | 8/2004 | Hasebe et al. |
| 2006/0205600 | A1 | 9/2006 | Otsubo et al. |
| 2008/0182756 | A1 | 7/2008 | Kozuki et al. |
| 2009/0081307 | A1 | 3/2009 | Tsuda |
| 2010/0204283 | A1 | 8/2010 | Dairiki et al. |

FOREIGN PATENT DOCUMENTS

| CN | 101233847 A | 8/2008 |
| CN | 101379974 A | 3/2009 |
| JP | 54-23123 | 2/1979 |
| JP | 54023123 A * | 2/1979 |
| JP | 57-35504 A | 2/1982 |
| JP | 60-84201 A | 5/1985 |
| JP | 5-43403 A | 2/1993 |
| JP | 9-278605 A | 10/1997 |
| JP | 9-309801 A | 12/1997 |
| JP | 2000-1404 A | 1/2000 |
| JP | 2003-319643 A | 11/2000 |
| JP | 2001-513530 A | 9/2001 |
| JP | 2002-249403 A | 9/2002 |
| JP | 2004-300073 A | 10/2004 |
| JP | 2005-22984 A | 1/2005 |
| JP | 2005022984 A * | 1/2005 |
| JP | 2006-248994 A | 9/2006 |
| JP | 2006-257072 A | 9/2006 |
| JP | 2008-184455 A | 8/2008 |
| WO | WO 95/17817 A1 | 7/1995 |
| WO | WO 95/31903 A1 | 11/1995 |
| WO | WO 2009/028454 A1 | 3/2009 |

OTHER PUBLICATIONS

International Search Report for PCT/JP2011/069863 dated Dec. 6, 2011.
Chinese Office Action and English translation dated Apr. 17, 2014 for Application No. 201180052202.5.
Machine-Generated Translation for JP-2000-319643-A, published Nov. 21, 2000.
Machine-Generated Translation for JP-2005-22984-A, published Jan. 27, 2005.
Machine-Generated Translation for JP-54-23123-A, published Feb. 21, 1979.
Machine-Generated Translation for JP-9-278605-A, published Oct. 28, 1997.
Machine-Generated Translation for JP-9-309801-A, published Dec. 2, 1997.
International Preliminary Report on Patentability for International Patent Application No. PCT/JP2011/069863, dated Apr. 9, 2013.

* cited by examiner

*Primary Examiner* — Sreenivasan Padmanabhan
*Assistant Examiner* — Courtney A Brown
(74) *Attorney, Agent, or Firm* — Birch, Stewart, Kolasch & Birch, LLP

(57) ABSTRACT

The present invention provides the efficacy-enhancing agent composition for an agricultural chemical containing at least one compound (A) selected from specific ethoxylate compounds, specific polyoxyethylene fatty acid esters, specific polyoxyethylene sorbitan fatty acid esters, specific (poly) glycerol fatty acid esters, and specific alkyl saccharides; and at least one compound (B) selected from specific polyoxyalkylene alkyl ethers and specific aliphatic alcohols.

12 Claims, No Drawings

METHOD FOR PRODUCING AN AGRICULTURAL PRODUCT

FIELD OF THE INVENTION

The present invention relates to an efficacy-enhancing agent composition for agricultural chemicals and an agricultural chemical composition.

BACKGROUND OF THE INVENTION

Various surfactants have been conventionally used in agricultural chemical-containing compositions in order to fully achieve agricultural chemical effects. For example, it is known that an anionic surfactant enhances the effect of a bipyridinium herbicide in combination with a chelating agent in an agricultural chemical-containing composition (e.g., see WO 95/31903 A). It is known that an agricultural chemical-containing composition having a high agricultural chemical activity is obtained from a cationic surfactant and addition of a chelating agent and another surfactant (e.g., see WO 95/17817 A). In addition, there has been a proposed non-aqueous spreading agent for increasing wettability, prepared by dissolving a sorbitan fatty acid ester, polyoxyethylene alkyl ether and a polyether-modified silicone in isopropyl alcohol (see JP-A2000-001404 (Claims and other sections)). JP-A2006-248994 discloses a spreading agent composition for a non-aqueous agricultural chemical, containing a surfactant, a water-miscible organic solvent having a flash point of not lower than 70° C., and an anti-foaming or defoaming agent. JP-A2006-257072 discloses a herbicide composition containing a polyoxyalkylene fatty acid ester and other nonionic surfactant. JP-A2008-184455 discloses a liquid agricultural chemical formulation containing a hydrophobic compound having an agricultural chemical activity, a specific nonionic surfactant selected from polyoxyethylene-polyoxypropylene block copolymers etc. an anionic surfactant, a specific ether compound and 1,3-dimethyl-2-imidazolidinone in respective specified amounts. JP-A2002-249403 discloses an efficacy-enhancing agent for agricultural chemicals, containing at least one compound selected from the group having specific alcohol, ether, and ester compounds as an effective component.

SUMMARY OF THE INVENTION

The present invention relates to a method for producing an agricultural product, including a step of applying an agricultural chemical composition containing (A) at least one compound selected from the following (A1) to (A5); (B) at least one compound selected from the following (B1) to (B2); and an agricultural chemical ingredient selected from active ingredients in bactericides, pesticides, miticides, herbicides and plant growth regulators to a subject sensitive to the agricultural chemical ingredient:

(A1): a polyoxyethylene alkyl ether represented by the formula (A1):

$$R^{1a}O\text{-}(EO)_l\text{—}R^{2a} \quad (A1)$$

wherein, $R^{1a}$ represents a linear or branched, alkyl or alkenyl group having 10 to 16 carbon atoms; EO represents an ethyleneoxy group; l represents an average mole number of ethyleneoxy groups added, ranging from 3 to 40; and $R^{2a}$ represents a hydrogen atom or a methyl group, (A2): a polyoxyethylene fatty acid ester, wherein a fatty acid group has 8 to 16 carbon atoms; and an average number of moles of ethylene oxide added per mole of fatty acid is 5 to 40, (A3): a polyoxyethylene sorbitan fatty acid ester, wherein a fatty acid group has 8 to 16 carbon atoms; and an average number of moles of ethylene oxide added per mole of fatty acid is 5 to 40, (A4): a (poly)glycerol fatty acid ester, wherein a fatty acid group has 8 to 16 carbon atoms; and an average condensation degree of glycerol is 1 to 3, and (A5): an alkyl saccharide represented by the formula (A5):

$$R^{3a}\text{—}O\text{-}(G)_p \quad (A5)$$

wherein $R^{3a}$ represents an alkyl group having 8 to 16 carbon atoms; G represents a reducing sugar group having 5 to 6 carbon atoms; and p represents a number of 1 to 10;

(B1): a polyoxyalkylene alkyl ether represented by the formula (B1):

$$R^{1b}O\text{—}[(PO)_m/(EO)_n]\text{—}R^{2b} \quad (B1)$$

wherein, $R^{1b}$ represents a linear or branched, alkyl or alkenyl group having 6 to 12 carbon atoms; PO represents a propyleneoxy group; 30 represents an ethyleneoxy group; m represents an average mole number of propyleneoxy groups added, ranging from 1 to 25; n represents an average mole number of ethyleneoxy groups added, ranging from 0 to 4; and $R^{2b}$ represents a hydrogen atom or a methyl group; wherein "/" means that PO and EO groups may be arranged at random or in blocks, and (B2): an aliphatic alcohol represented by the formula (B2):

$$R^{3b}\text{—}OH \quad (B2)$$

wherein $R^{3b}$ represents a linear or branched, alkyl group having 8 to 14 carbon atoms.

The present invention also provides use of a composition containing compounds (A) and (B) as an agricultural spreading agent composition.

The present invention further provides a method for efficacy-enhancing an agricultural chemical ingredient selected from active ingredients in bactericides, pesticides, miticides, herbicides and plant growth regulators, including mixing the agricultural chemical ingredient with compounds (A) and (B).

DETAILED DESCRIPTION OF THE INVENTION

Methods described in the above shown patent publications sometimes fail to achieve sufficient effects of an agricultural chemical due to, for example, an insufficient wetting and spreading of drops of the agricultural chemical on leaves of a plant in application to leaves.

The present invention provides an efficacy-enhancing agent composition for an agricultural chemical that can improve wetting and spreading performances of agricultural chemicals and effectively efficacy-enhancing an agricultural chemical.

According to the present invention, provided are a efficacy-enhancing agent composition of an agricultural chemical and an agricultural chemical composition that can improve wetting and spreading performances of agricultural chemicals and efficacy-enhancing an agricultural chemical effectively.

The present invention includes the following aspects: (1) a method for producing an agricultural product, including a step of applying an agricultural chemical composition containing the compound (A), the compound (B) that is either compound (B1) or (B2), and an agricultural chemical ingredient selected from active ingredients in bactericides, pesticides, miticides, herbicides and plant growth regulators to a subject sensitive to the agricultural chemical ingredient; (2) an efficacy-enhancing agent composition for an agricultural chemical, containing the compound (A) [hereinafter, referred to as compound (A)]; and the compound (B) [hereinafter, referred to as compound (B)]; (3) an agricultural chemical composition, containing the compound (A), the compound (B), and an agricultural chemical ingredient selected from active ingredients in bactericides, pesticides, miticides, herbicides and plant growth regulators; (4) a method for cultivating a plant, including a step of applying the efficacy-enhancing agent composition for an agricultural chemical of the present invention and an agricultural chemical ingredient selected from active ingredients in bactericides, pesticides, miticides, herbicides and plant growth regulators to the plant; (5) a method for cultivating a plant, including a step of applying the agricultural chemical composition of the present invention to the plant; (6) an efficacy-enhancing agent composition for an agricultural chemical, containing compounds (A) and (B), in which the compound (A) is represented by the formula (A1) and the compound (B) is represented by the formula (B1); and (7) an efficacy-enhancing agent composition for an agricultural chemical, containing compounds (A) and (B), in which the compound (B) is represented by the formula (B1).

The efficacy-enhancing agent composition of the present invention contains compounds (A) and (B). The reason of a combination of compounds (A) and (B) improved in wetting and spreading performances of an agricultural chemical is unknown, but assumed that the compound (B) adsorbing in an interface between a drop of the composition and a leaf to reduce an interfacial tension and the compound (A) reducing a surface tension of a drop of liquid by itself own are similar in structures and interact with each other, thereby dramatically improving these properties.

<Compound (A)>

The efficacy-enhancing agent composition of the present invention contains at least one compound (A) selected from the following (A1) to (A5) for improving wetting and spreading performances and efficacy-enhancing an agricultural chemical. When the compound (B) is the compound (B1), for improving wetting and spreading performances and efficacy-enhancing an agricultural chemical, at least one compound (A) is preferably selected from compounds (A1), (A4), and (A5), and more preferably compounds (A1) and (A5). When the compound (B) is the compound (B2), for improving wetting and spreading performances and efficacy-enhancing an agricultural chemical, at least one compound (A) is preferably selected from compounds (A1), (A2), and (A4), and more preferably compounds (A1) and (A4).

The compound (A1) is represented by the formula (A1).

$$R^{1a}O\text{-}(EO)_l\text{—}R^{2a} \qquad (A1)$$

For improving wetting and spreading performances and efficacy-enhancing an agricultural chemical, in the formula (A1), $R^{1a}$ represents a linear or branched alkyl or alkenyl group having 10 to 16 carbon atoms, preferably having 10 to 14 carbon atoms, more preferably having 10 to 12 carbon atoms, even more preferably having 12 carbon atoms, and still even more preferably a linear alkyl group having 12 carbon atoms. "l" represents an average mole number of ethyleneoxy (EO) groups added, and for improving wetting and spreading performances and efficacy-enhancing an agricultural chemical, ranges from 3 to 40, preferably 4 to 30, more preferably 4 to 25, more preferably 5 to 20, more preferably 5 to 15, more preferably 5 to 12, and even more preferably 5 to 10. For improving wetting and spreading performances and efficacy-enhancing an agricultural chemical, $R^{2a}$ represents a hydrogen atom or a methyl group, and preferably a hydrogen atom.

The compound (A2) is a polyoxyethylene fatty acid ester. For improving wetting and spreading performances and efficacy-enhancing an agricultural chemical, in the compound (A2), a fatty acid group has 8 to 16 carbon atoms, preferably 10 to 14 carbon atoms, and more preferably 10 to 12 carbon atoms. The fatty acid group preferably has a linear or branched alkyl or alkenyl group, and more preferably a linear alkyl group. Examples of a fatty acid for the fatty acid group include caprylic acid, capric acid, lauric acid, myristic acid and palmitic acid. For improving wetting and spreading performances and efficacy-enhancing an agricultural chemical, in the compound (A2), an average number of moles of ethylene oxide added per mole of fatty acid is 5 to 40, preferably 5 to 20, and more preferably 6 to 15. The polyoxyethylene fatty acid ester is preferably a monoester compound.

The compound (A3) is a polyoxyethylene sorbitan fatty acid ester. For improving wetting and spreading performances and efficacy-enhancing an agricultural chemical, in the compound (A3), a fatty acid group has 8 to 16 carbon atoms, preferably 10 to 14 carbon atoms, and more preferably 10 to 12 carbon atoms. The fatty acid group preferably has a linear or branched alkyl or alkenyl group, and more preferably a linear alkyl group. Examples of a fatty acid for the fatty acid group of compound (A3) include caprylic acid, capric acid, lauric acid, myristic acid and palmitic acid. For improving wetting and spreading performances and efficacy-enhancing an agricultural chemical, in the compound (A3), average number of moles of ethylene oxide added per mole of fatty acid is 5 to 40, preferably 5 to 20, and more preferably 6 to 15. The compound (A3) preferably has a degree of esterification of 1.

The compound (A4) is a (poly)glycerol fatty acid ester. As used herein, the "(poly)glycerol" refers to "glycerol or polyglycerol". For improving wetting and spreading performances and efficacy-enhancing an agricultural chemical, in the compound (A4), a fatty acid group has 8 to 16 carbon atoms, preferably 8 to 12 carbon atoms, more preferably 10 to 12 carbon atoms, and even more preferably 12 carbon atoms. The fatty acid group preferably has a linear or branched alkyl or alkenyl group, and more preferably a linear alkyl group. Examples of a fatty acid for the fatty acid group of compound (A4) include caprylic acid, capric acid, lauric acid, myristic acid and palmitic acid. For improving wetting and spreading performances and efficacy-enhancing an agricultural chemical, in the compound (A4), an average condensation degree of glycerol is 1 to 3, preferably 1 to 2, and more preferably 2.

The compound (A5) is an alkyl saccharide represented by the formula (A5).

$$R^{3a}\text{—}O\text{-}(G)_p \qquad (A5)$$

For improving wetting and spreading performances and efficacy-enhancing an agricultural chemical, in the formula (A5), $R^{3a}$ represents an alkyl group having 8 to 16 carbon atoms, and preferably 10 to 14 carbon atoms. G represents a reducing sugar group having 5 to 6 carbon atoms such as those derived from ribose, arabinose, xylose, allose, altrose, glucose, mannose, fructose, gulose, idose, galactose, and talose, preferably derived from glucose, mannose, fructose, and galactose, and more preferably derived from glucose.

For improving wetting and spreading performances and efficacy-enhancing an agricultural chemical, p represents the number of 1 to 10, and preferably 1 to 5.

<Compound (B1)>

The compound (B1) is represented by the formula (B1).

$$R^{1b}O-[(PO)_m/(EO)_n]-R^{2b} \quad (B1)$$

For improving wetting and spreading performances and efficacy-enhancing an agricultural chemical, in the formula (B1), $R^{1b}$ represents a linear or branched alkyl or alkenyl group having 6 to 12 carbon atoms, preferably 8 to 12 carbon atoms, more preferably 8 to 10 carbon atoms, and even more preferably a linear alkyl group having 8 to 10 carbon atoms. "m" represents an average mole number of propyleneoxy (PO) groups added, and for improving wetting and spreading performances and efficacy-enhancing of an agricultural chemical, ranges from 1 to 25, preferably 2 to 20, more preferably 2 to 20, more preferably 2 to 18, more preferably 2 to 16, more preferably 2 to 12, and even more preferably 2 to 10. "n" represents an average mole number of ethyleneoxy (EO) groups added, and for improving wetting and spreading performances and efficacy-enhancing an agricultural chemical, ranges from 0 to 4, preferably 0 to 3, more preferably 0 to 2, even more preferably 0 to 1, and still even more preferably 0. For improving wetting and spreading performances and efficacy-enhancing an agricultural chemical, in the formula (B1), a ratio of m to the sum of m and n, m/(m+n), is preferably 0.5 to 1.0, more preferably 0.6 to 1.0, more preferably 0.7 to 1.0, more preferably 0.8 to 1.0, more preferably 0.9 to 1.0, and even more preferably 1.0. For improving wetting and spreading performances and efficacy-enhancing of an agricultural chemical, $R^{2b}$ represents a hydrogen atom or a methyl group, and preferably a hydrogen atom. In cases of the compound (B1) containing both PO and EO, for improving wetting and spreading performances and efficacy-enhancing of an agricultural chemical, PO and EO are preferably arranged in blocks, and more preferably in the order of $R^{1b}O-$, a PO block, and an EO block.

<Compound (B2)>

The compound (B2) is represented by the formula (B2).

$$R^{3b}-OH \quad (B2)$$

For improving wetting and spreading performances and efficacy-enhancing of an agricultural chemical, in the formula (B2), $R^{3b}$ represents a linear or branched alkyl group having 8 to 14 carbon atoms, preferably 8 to 12 carbon atoms, more preferably 8 to 10 carbon atoms, and even more preferably a linear alkyl group having 10 carbon atoms.

<Composition etc. Of the Efficacy-Enhancing Agent Composition for an Agricultural Chemical>

In the efficacy-enhancing agent composition of the present invention, a weight ratio of compounds (A) to (B), (A)/(B), is preferably 0.03 to 30, more preferably 0.05 to 20, more preferably 0.1 to 10, more preferably 0.2 to 9, more preferably 0.2 to 8, more preferably 0.3 to 8, and even more preferably 0.5 to 2. When the weight ratio (A)/(B) is within the above shown range, the wetting and spreading performances on plants and the agricultural chemical penetration of the spray liquid are good and a good efficacy-enhancing of an agricultural chemical is obtained.

The efficacy-enhancing agent composition of the present invention preferably contains compounds (A) and (B) in the total amount of not less than 5% by weight, more preferably not less than 10% by weight, more preferably not less than 20% by weight, more preferably not less than 40% by weight, more preferably not less than 60% by weight, more preferably not less than 80% by weight, and even more preferably not less than 90% by weight. The possible upper limit is 100% by weight. When the total amount of compounds (A) and (B) is within the above shown range, concentrations of compounds (A) and (B) are sufficient and a good efficacy-enhancing of an agricultural chemical is obtained when they are diluted in use together with an agricultural chemical. In results, a good efficacy-enhancing of an agricultural chemical is obtained. Therefore, they can be used with a usual diluting magnification of an agricultural chemical to achieve the efficacy-enhancing of an agricultural chemical, which is preferable also in view of cost and workability.

In addition, the present invention can further use other surfactant than compounds (A) and (B) within the range that does not impair effects of these compounds. Examples of the other surfactant include nonionic, anionic, cationic, and amphoteric surfactants other than compounds (A) and (B), and mixtures thereof.

In cases of using the other surfactant together with compounds (A) and (B), an amount of the other surfactant can be arbitrarily determined within the range that does not impair effects of these compounds. However, for improving wetting and spreading performances and efficacy-enhancing of an agricultural chemical, in the efficacy-enhancing agent composition, a proportion of compounds (A) and (B) is preferably not less than 50% by weight, more preferably not less than 70% by weight, and even more preferably not less than 90% by weight of the total surfactants.

Examples of the nonionic surfactant include polyoxyethylene alkyl ethers [excluding those corresponding to the formula (A1) or (B1)], polyoxyethylene alkylaryl ethers, polyoxyethylene alkylaryl ether-formaldehyde condensates, polyoxyalkylene aryl ethers, polyoxyalkylene alkyl sorbitol esters, polyoxyalkylene alkyl glycerol esters, polyoxyalkylene block copolymers, polyoxyalkylene block copolymer alkyl glycerol esters, polyoxyalkylene alkylsulfonamide, polyoxypropylene block copolymers, polyoxyethylene oleyl ethers, polyoxyalkylene alkylphenols, and polyoxyalkylene alkyl polyglucosides, and mixtures of two or more of them.

Examples of the cationic surfactant include alkylamine-ethylene oxide adducts and alkylamine-propylene oxide adducts such as tallowamine-ethylene oxide adducts, oleylamine-ethylene oxide adducts, soyamine-ethylene oxide adducts, cocoamine-ethylene oxide adducts, synthetic alkylamine-ethylene oxide adducts, and octylamine-ethylene oxide adducts, and dialkylamine derivatives, and mixtures thereof. Examples of the dialkylamine derivative include dialkyl monomethyl hydroxyethyl ammonium propionates, dialkyl monomethyl benzalkonium chlorides, dialkyl monomethyl ethyl ammonium ethyl sulfates, dialkyl monomethyl amine oxides, dialkyl monomethyl amino carboxybetaines, and dialkyl monomethyl hydroxy sulfobetaines.

For improving wetting and spreading performances and efficacy-enhancing of an agricultural chemical, preferred cationic surfactants are alkylamine-ethylene oxide adducts, alkylamine-propylene oxide adducts, and dialkylamine derivatives, and more preferred are tallowamine-ethylene oxide adducts and dilauryl monomethyl benzalkonium chloride.

Typical anionic surfactants are available in the form of an aqueous solution or solid. Examples thereof include mono- and dialkylnaphthalenesulfonic acids sodium salts, α-olefinsulfonic acid sodium salt, alkanesulfonic acid sodium salts, alkylsulfosuccinates, alkylsulfates, polyoxyalkylene alkyl ether sulfates, polyoxyalkylene alkyl aryl ether sulfates, polyoxyalkylene styryl phenyl ether sulfates, monoand dialkylbenzenesulfonates, alkylnaphthalene sulfonates, alkylnaphthalene sulfonate-formaldehyde condensates, alkyl diphenyl ether sulfonates, olefinic sulfonates, mono- and dialkylphosphates, polyoxyalkylene mono- and dialkylphosphates, polyoxyalkylene mono- and diphenyl ether phosphates, polyoxyalkylene mono- and dialkylphenyl ether phosphates, polycarboxylates, salts of fatty acids, linear and branched alkyl polyoxyalkylene ether acetic acids and salts thereof, alkenylpolyoxyalkylene ether acetic acids and salts thereof, linear and branched alkylamide polyoxyalkylene ether acetic acids and salts thereof, stearic acid and salts thereof, oleic acid and salts thereof, N-methylfatty acid taurides, and mixtures of two or more of them (including sodium, potassium, ammonium and amine salts). For improvement of emulsifying and dispersing, the anionic surfactant is preferably selected from fatty acid salts, more preferably from sodium and potassium salts of higher fatty acids such as of oleic acid, and castor oil fatty acid, and even more preferably potassium oleate.

Examples of the amphoteric surfactant include lauryldimethylamine oxide, Armox C/12, amine oxide, Monaterics, Miranols, betaines, Lonzaines, and other amine oxides, and mixtures thereof.

The efficacy-enhancing agent composition of the present invention may be composed of compounds (A) and (B), or compounds (A) and (B) and other component(s). In the latter case, the rest part of the composition is preferably water and/or an organic solvent. The composition containing water and/or an organic solvent has better stability at low or high temperature and long-term storage stability. In addition, the composition containing water and/or an organic solvent can be diluted to easily disperse and dissolve compounds (A) and (B) in a diluting medium (water and/or an organic solvent) to enhance effects of efficacy-enhancing of an agricultural chemical. Preferred examples of the organic solvent include isobutanol, isopropanol, ethanol, diethylene glycol, ethyl lactate, butyl cellosolve, polyethylene glycol (weight average molecular weight: 200 to 400), dimethylsulfoxide, N-butyl carbitol, 1,3-butylene glycol, dipropylene glycol, 2-(2-methoxyethoxy)ethanol, and ethyl carbitol. For improving wetting and spreading performances and efficacy-enhancing an agricultural chemical, preferably used are ethyl lactate and diethylene glycol, and more preferably used is diethylene glycol.

In the efficacy-enhancing agent composition of the present invention, a content of water and/or an organic solvent is not specifically limited. However, the content is preferably such that compounds (A) and (B) accounts for not less than 50% by weight, more preferably not less than 70% by weight, and even more preferably not less than 90% by weight of the efficacy-enhancing agent composition. The content is preferably less than 50% by weight, for example, from 1% by weight to less than 50% by weight, and more preferably from 5 to 30% by weight of the composition.

<Agricultural Chemical Composition>

The agricultural chemical composition of the present invention contains compounds (A) and (B) as described above and an agricultural chemical ingredient. As used herein, the "agricultural chemical ingredient" refers to an active component in an agricultural chemical. The agricultural chemical composition of the present invention thus includes the efficacy-enhancing agent composition of the present invention and an agricultural chemical ingredient selected from active ingredients in bactericides, pesticides, miticides, herbicides and plant growth regulators. Considering effects on agricultural products, the agricultural chemical composition of the present invention has preferably a low content of one or more compounds selected from (i) hydrogen peroxide and compounds generating hydrogen peroxide in water and (ii) hypochlorous acid, hypochlorites, and compounds generating hypochlorous acid in water. For example, the agricultural chemical composition of the present invention preferably contains hypochlorous acid or hydrogen peroxide in an amount of not more than 0.1% by weight, more preferably not more than 0.01% by weight, and even more preferably no hypochlorous acid or hydrogen peroxide. This applies to the agricultural chemical preparation and the agricultural chemical preparation for spraying described below.

In the agricultural chemical composition of the present invention, for improving wetting and spreading performances and efficacy-enhancing of an agricultural chemical, a weight ratio of the compound (A) to the agricultural chemical ingredient, compound (A)/agricultural chemical ingredient, is preferably 0.05 to 50, and more preferably 0.1 to 10.

In the agricultural chemical composition of the present invention, for improving wetting and spreading performances and efficacy-enhancing of an agricultural chemical, a weight ratio of the compound (B) to the agricultural chemical ingredient, compound (B)/agricultural chemical ingredient, is preferably 0.05 to 50, more preferably 0.1 to 20, and even more preferably 0.1 to 10.

In the agricultural chemical composition of the present invention, for improving wetting and spreading performances and efficacy-enhancing an agricultural chemical, a weight ratio of the total of compounds (A) and (B) to the agricultural chemical ingredient, (compounds (A) and (B))/(agricultural chemical ingredient), is preferably 0.1 to 100, more preferably 0.2 to 40, and even more preferably 0.2 to 20.

The agricultural chemical composition of the present invention can be in any preparation form, including emulsion, liquid, wettable powder, granule, powder, and flowable concentrate. The agricultural chemical composition thus may contain other additive according to its preparation form, including an emulsifier, a solvent, a dispersant, and a carrier. The efficacy-enhancing agent composition according to the present invention can be used in an agricultural chemical composition in each of the above shown preparation forms containing the efficacy-enhancing agent composition for an agricultural chemical. Then when an agricultural chemical containing no efficacy-enhancing agent composition is diluted and used, the efficacy-enhancing agent composition of the present invention, separately supplied, can be used. In either of these cases, the efficacy-enhancing agent composition of the present invention can provide the intended effects of the efficacy-enhancing.

The preparation of the agricultural chemical composition of the present invention may further contain a chelating agent, a pH adjusting agent, an inorganic salt, and/or a thickener as necessary.

Examples of the chelating agent that can be used in the present invention include aminopolycarboxylic acid chelating agents, aromatic and aliphatic carboxylic acid chelating agents, amino acid chelating agents, ether polycarboxylic acid chelating agents, phosphonic acid chelating agents (e.g., iminodimethylphosphonic acid (IDP) and alkyldiphosphonic acid (ADPA)), dimethylglyoxime (DG), hydroxycarboxylic acid chelating agents, and polyelectrolyte (including oligoelectrolyte) chelating agents. These agents may be used in a free acid form or a salt form such as of sodium, potassium, and ammonium. The chelating agent is added in an amount of 0.01 to 30 mole times as much as the amount of the component (B) in the efficacy-enhancing agent composition.

Any aminopolycarboxylic acid chelating agent can be used, including:
a) $RNX_2$-type compounds,
b) $NX_3$-type compounds,
c) R—NX—$CH_2CH_2$—NX—R-type compounds,
d) R—NX—$CH_2CH_2$—$NX_2$-type compounds, and
e) $X_2N$—R'—$NX_2$-type compounds,
wherein, X represents —$CH_2COOH$ or —$CH_2CH_2COOH$; R represents a hydrogen atom, an alkyl group, a hydroxy group, a hydroxyalkyl group, or a group representing such a known chelating compound;
R' represents an alkylene group, a cycloalkylene group, or a group representing such a known chelating compound. Typical examples of this chelating agent include ethylenediaminetetraacetic acid (EDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), N-(2-hydroxyethyl)ethylenediaminetriacetic acid (EDTA-OH), and glycol ether diamine tetraacetic acid (GEDTA), and salts thereof.

Examples of the chelating agent that can be used in the present invention include: for aromatic and aliphatic carboxylic acid chelating agents, oxalic acid, succinic acid, pyruvic acid, anthranilic acid, and salts thereof; for amino acid chelating agents, glycine, serine, alanine, lysine, cystine, cysteine, ethionine, tyrosine, and methionine, and salts and derivatives thereof; for hydroxycarboxylic acid chelating agents, glycolic acid, malic acid, citric acid, gluconic acid, heptonic acid, acetic acid, and salts thereof; and for ether polycarboxylic acid chelating agents, compounds represented by the following formula and analogues thereof and salts thereof (preferably Na salt or the like) thereof.

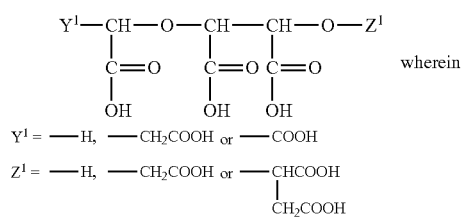

[Formula 1]

wherein
$Y^1$ = —H, —$CH_2COOH$ or —COOH
$Z^1$ = —H, —$CH_2COOH$ or —CHCOOH
                                          |
                                          $CH_2COOH$ Examples of the polyelectrolyte (including oligoelectrolyte) chelating agent that can be used in the present invention include acrylic acid polymers, maleic anhydride polymers, α-hydroxyacrylic acid polymers, itaconic acid polymers, and copolymers thereof, and epoxysuccinic acid polymers.

Examples of the pH adjusting agent that can be used in the present invention include citric acid, phosphoric acid (pyrophosphoric acid), gluconic acid, or salts thereof.

Examples of the inorganic salt that can be used in the present invention include inorganic mineral salts such as inorganic clay, talc, bentonite, zeolite, calcium carbonate, diatomite, and white carbon, and inorganic ammonium salts such as ammonium sulfate, ammonium nitrate, ammonium phosphate, ammonium thiocyanate, ammonium chloride, and ammonium sulfamate.

Any thickener can be used in the present invention, including natural, semisynthetic, and synthetic water-soluble thickeners. Specific examples of the thickener include: for natural viscous substances, microorganism-derived xanthane gum and Zanflow, and plant-derived pectin, gum arabic, and guar gum; for semisynthetic viscous substances, methylated, carboxyalkylated, and hydroxyalkylated celluloses and starch derivatives (including methylcellulose, carboxymethylcellulose, and hydroxymethylcellulose), and sorbitol; and for synthetic viscous substances, polyacrylates, polymaleates, polyvinylpyrrolidone, and pentaerythritol-ethylene oxide adducts.

Examples of the agricultural chemical ingredient in the agricultural chemical composition of the present invention include, but not limited to, those described in "Nouyaku handobukku 2001 nendoban (Agricultural chemical handbook 2001 edition)" (Japan Plant Protection Association). The efficacy-enhancing agent composition of the present invention has no harmful effects on various agricultural products and can be used safely.

Examples of the bactericide include sulfur-based zineb (zinc ethylenebisdithiocarbamate), maneb (manganese ethylenebisdithiocarbamate), manzeb (manganese-zinc ethylenebisdithiocarbamate), and polycarbamate (bisdimethyldithiocarbamoylzinc ethylenebisdithiocarbamate); benzimidazole-based benomyl (methyl-1-(butylcarbamoyl)-2-benzimidazole carbamate) and thiophanate-methyl (1,2-bis(3-methoxycarbonyl-2-thioureido)benzene); dicarboximide-based vinclozolin (3-(3,5-dichlorophenyl)-5-methyl-5-vinyl-1,3-oxazolidine-2,4-dione), iprodione (3-(3,5-dichlorophenyl)-N-isopropyl-2,4-dioxoimidazolidine-1-carboxamide), and procymidone (N-(3,5-dichlorophenyl)-1,2-dimethylcyclopropane-1,2-dicarboximide); and others such as triazine (2,4-dichloro-6-(2-chloroanilino)-1,3,5-triazine), triflumizole((E)-4-chloro-α,α,α-trifluoro-N-(1-imidazole-1-yl-2-propoxyethylidene)-o-toluidine), iminoctadine acetate (1,1-iminodi(octamethylene) diguanidinium=triacetate), an organocopper compound (Oxine-copper), cupric hydroxide (e.g., Kocide Bordeaux mixture), antibiotic bactericides (streptomycins, tetracyclins, polyoxy-type bactericides, Blasticidin S, kasugamycins, and validamycins), triadimefon (1-(4-chlorophenoxy)-3,3-dimethyl-1-(1,2,4-triazole-1-yl)-2-butanone), isoprothiolane (diisopropyl-1,3-dithiolan-2-ylidenemalonate), and TPN (tetrachloroisophthalonitrile). Among these bactericides, preferred are an organocopper compound (Oxine-copper), cupric hydroxide, triflumizole((E)-4-chloro-α,α,α-trifluoro-N-(1-imidazole-1-yl-2-propoxyethylidene)-o-toluidine), iprodione (3-(3,5-dichlorophenyl)-N-isopropyl-2,4-dioxoimidazolidine-1-carboxamide).

Examples of the pesticide include: pyrethroid pesticides such as permethrin ((3-phenoxybenzyl (1RS,3RS)-(1RS,3RS)-3-(2,2-dichlorovinyl)-2,2-dimethylcyclopropane carboxylate), cypermethrin ((RS)-α-cyano-3-phenoxybenzyl (1RS,3RS)-(1RS,3RS)-3-(2,2-dichlorovinyl)-2,2-dimethylcyclo propanecarboxylate), and fenvalerate (α-cyano-3-phenoxybenzyl-2-(4-chlorophenyl)-3-methylbutanoate); organophosphorus pesticides such as DDVP (dimethyl 2,2-dichlorovinylphosphate), sumithion (MEP) (O,O-dimethyl-O-(3-methyl-4-nitrophenyl)thiophosphate), Malathon (S-[1,2,-bis(ethoxycarbonyl)ethyl] dimethylphosphorothiolthionate), dimethoate (dimethyl S-(N-methylcarbamoylmethyl)dithiophosphate), Elsan (S-[α-(ethoxycarbonyl)benzyl]dimethylphosphorothiolthionate), Baycid (O,O-dimethyl-O-(3-methyl-4-methylthiophenylthiophosphate)); and carbamate pesticides such as Bassa (O-sec-butylphenyl methylcarbamate), MTMC (m-tolyl methylcarbamate), Meobal ((3,4-dimethylphenyl) N-methylcarbamate), and methomyl (S-methyl N-[(methylcarbamoyl)oxy]thioacetimide). Among these pesticides, preferred are permethrin, DDVP (dimethyl 2,2-dichlorovinylphosphate), and methomyl (S-methyl N-[(methylcarbamoyl)oxy]thioacetimide).

Examples of the natural pesticide include pyrethrin and piperonyl butoxide compositions of pyrethrum origin, and rotenone and nicotinic (3-(1-methyl-2-pyrrolidinyl)pyridine sulfate) compositions of derris origin, which is a leguminous plant. Examples of an insect growth regulator (IGR agent) include diflubenzuron (1-(4-chlorophenyl)-3-(2,6-difluorobenzoyl)urea), teflubenzuron (1-(3,5-dichloro-2,4-difluorophenyl)-3-(2,6-difluorobenzoyl) urea), and chlorfluazuron (1-[3,5-dichloro-4-(3-chloro-5-trifluoromethyl-2-pyridyloxy)phenyl]-3-(2,6-difluorobenzoyl)urea.

Examples of the miticide include CPCBS (p-chlorophenyl p-chlorobenzenesulfonate), phenisobromolate (4,4'-dibromobenzilic acid isopropyl ester), tetradifon (2,4,5,4'-tetrachlorodiphenylsulfone), fenothiocarb (S-4-phenoxybutyl dimethylthiocarbamate), fenpyroximate (tert-butyl (E)-α-(1,3-dimethyl-5-phenoxypyrazol-4-ylmethyleneaminooxy-p-toluate), fluazinam (3-chloro-N-(3-chloro-5-trifluoromethyl-2-pyridyl)-α,α,α-trifluoro-2,6-dinitro-p-toluidine), fenbutatin oxide (hexakis(β,β-dimethylphenylethyl)distannoxane), hexythiazox (trans-5-(4-chlorophenyl)-N-cyclohexyl-4-methyl-2-oxothiazolidine-3-carboxamide), and amitraz(3-methyl-1,5-bis(2,4-xylyl)-1,3,5-triazapenta-1,4-diene). Among these miticides, preferred are phenisobromolate (4,4'-dibromobenzilic acid isopropyl ester), amitraz(3-methyl-1,5-bis(2,4-xylyl)-1,3,5-triazapenta-1,4-diene), and fenpyroximate (tert-butyl (E)-α-(1,3-dimethyl-5-phenoxypyrazol-4-ylmethyleneaminooxy)-p-toluate).

Examples of the herbicide include: acid amide herbicides such as Stam (3,4-dichloropropionanilide, DCPA); urea herbicides such as DCMU (3-(3,4-dichlorophenyl)-1,1-dimethylurea); dipyridyl herbicides such as paraquat (1,1'-dimethyl-4,4'-bipyridinium dichloride) and diquat (6,7-dihydrodipyrido[1,2-a:2',1'c]pyrazinediium dibromide); diazine herbicides such as bromacil (5-bromo-3-sec-butyl-6-methyluracil); triazine herbicides such as simazine (2-chloro-4,6-bis(ethylamino)-1,3,5-triazine); nitrile herbicides such as DBN (2,6-dichlorobenzonitrile); dinitroaniline herbicides such as trifluralin (α,α,α-trifluoro-2,6-dinitro-N,N-dipropyl-p-toluidine); carbamate herbicides such as benthiocarb (Saturn) (S-p-chlorobenzyl-N,N-diethylthiocarbamate); diphenyl ether herbicides such as NIP (2,4-dichlorophenyl p-nitrophenyl ether); phenol herbicides such as PCP (sodium pentachlorophenoxide); benzoic acid herbicides such as MDBA (3,6-dichloro-o-anisic acid dimethylamine); phenoxy herbicides such as 2,4-D sodium salt (sodium 2,4-dichlorophenoxyacetate); amino acid herbicides such as glyphosate (N-(phosphonomethyl)glycine and a salt thereof) and glufosinate (ammonium-DL-homoalanine-4-yl(methyl)-phosphinate); and aliphatic herbicides such as TCA-sodium (sodium trichloroacetate). Among these herbicides, preferred are DEN (2,6-dichlorobenzonitrile), DCMU (3-(3,4-dichlorophenyl)-1,1-dimethylurea), paraquat (1,1'-dimethyl-4,4'-bipyridinium dichloride), and diquat (6,7-dihydrodipyrido[1,2-a:2',1'c]pyrazinediium dibromide).

The agricultural chemical composition of the present invention can further contain one or more other agents such as plant growth regulators, fertilizers, and/or preservatives than those described above in combination.

Examples of the plant growth regulator include indolebutyric acid, ethychlozate (ethyl 5-chloro-3-(1H)indazolylacetate), benzylaminopurine (6-(N-benzylamino)purine), forchlorfenuron (1-(2-chloro-4-pyridyl)-3-phenylurea), gibberellin, decyl alcohol, and ethephon (2-chloroethylphosphonic acid).

In the present invention, for bactericidal, pesticidal, miticidal, or herbicidal purpose or purpose of control of plant growth, used is the agricultural chemical composition containing an agricultural chemical ingredient and the efficacy-enhancing agent composition of the present invention in an amount of 0.03 to 50 times, preferably 0.1 to 50 times, and more preferably 0.3 to 35 times the amount of the agricultural chemical ingredient.

In spraying the agricultural chemical composition of the present invention, a splay liquid of the agricultural chemical composition preferably contains compounds (A) and (B) in the total amount of 30 to 50000 ppm, more preferably 50 to 25000 ppm, more preferably 100 to 20000 ppm, more preferably 300 to 15000 ppm, more preferably 500 to 12000 ppm, and even more preferably 600 to 10000 ppm. The splay liquid containing compounds (A) and (B) in the total amount not lower than the lower limit forms liquid drops having good wetting and spreading performances on the surface of a plant and has a good agricultural chemical penetration to the plant, resulting in significant effects for efficacy-enhancing of an agricultural chemical. The splay liquid containing not more than the upper limit forms liquid drops having adequate wetting and spreading performances to attach to a plant and not to easily run off, thereby sufficiently achieving effects for efficacy-enhancing of an agricultural chemical. Note that, the rest part of the agricultural chemical composition is preferably water.

In spraying the agricultural chemical composition of the present invention, a splay liquid of the agricultural chemical composition containing compounds (A) and (B) within the range described above can be preferably sprayed at rate of 1 to 500 L/10a, more preferably 1 to 300 L/10a, more preferably 5 to 200 L/10a, more preferably 1 to 150 L/10a, more preferably 5 to 100 L/10a, more preferably 5 to 50 L/10a, and even more preferably 5 to 30 L/10a. The splay liquid sprayed at a rate not lower than the lower limit can sufficiently wet a subject, resulting in significant effects for efficacy-enhancing of an agricultural chemical. The splay liquid sprayed at a rate not more than the upper limit can adequately wet a subject and liquid drops of the splay liquid does not easily run off from a leaf. Therefore, according to the present invention, also provided is a method of spraying the agricultural chemical composition of the present invention (or an agricultural chemical preparation prepared from the agricultural chemical composition of the present invention) at a rate as described above, or a method for cultivating an agricultural product.

The agricultural chemical preparation containing the efficacy-enhancing agent composition of the present invention may be composed of individual packages of the efficacy-enhancing agent composition of the present invention and of an agricultural chemical component, or individual packages of compounds (A) and (B), of the other surfactant(s) than the components (A) and (B), and of an agricultural chemical composition. Note that, as used herein, the "individual package of an agricultural chemical component" refers to a package containing an agricultural chemical ingredient and any optional ingredient at any ratio in the form of emulsion, wettable powder or the like. Each individual package can be of any form and adequately prepared according to an intended use and purpose.

According to the present invention, provided is a method for producing an agricultural chemical composition, containing mixing compounds (A) and (B) and an agricultural chemical ingredient selected from active ingredients in bactericides, pesticides, miticides, herbicides and plant growth regulators. In this method, compounds (A) and (B) and the agricultural chemical ingredient are preferably used in proportions as described for the efficacy-enhancing agent composition for an agricultural chemical and the agricultural chemical composition.

In the method for producing an agricultural product of the present invention, the agricultural chemical composition of the present invention is used in the situation of using an agricultural chemical. The subject of the method of the present invention includes bacteria sensitive to bactericides, pests (insects) sensitive to pesticides, mites sensitive to miticides, weeds (not falling under the category of agricultural product) sensitive to herbicides, and agricultural products (plant to be cultivated) sensitive to plant growth regulators. The method can be applied to a single subject or multiple subjects. The method can be performed as targeting to a subject selected from plants, pests, and bacteria, for example, by spraying the agricultural chemical composition onto a farmland. In this case, plants include agricultural products and/or weeds.

The method for producing an agricultural product of the present invention contains a step of applying the efficacy-enhancing agent composition of the present invention and an agricultural chemical ingredient selected from active ingredients in bactericides, pesticides, miticides, herbicides and plant growth regulators to a subject sensitive to the agricultural chemical ingredient, or may contain a step of applying the agricultural chemical composition of the present invention to the subject. The subject can be treated with the efficacy-enhancing agent composition for an agricultural chemical, the agricultural chemical ingredient, or the agricultural chemical composition in any way, including the above-described direct spraying of a composition containing an agricultural chemical and the efficacy-enhancing agent composition for an agricultural chemical on a leaf, a stem, or a fruit or the like, and addition of a diluted agricultural chemical composition to a mineral nutrient solution or supplied water contacting with a root in hydroponics or cultivation in rock wool to supply (apply) to the surface of the root or the like. To effectively achieve effects of the efficacy-enhancing agent composition of the present invention (effects to enhance attachment of an active ingredient to a plant), application of the efficacy-enhancing agent composition or the agricultural chemical composition to a subject sensitive to an agricultural chemical ingredient is preferably conducted by spraying the efficacy-enhancing agent composition or the agricultural chemical composition on an aerial part of a plant, and more preferably on leaves. The efficacy-enhancing agent composition of the present invention and an agricultural chemical ingredient may also be separately applied to a subject sensitive to the agricultural chemical ingredient by the method as described above.

In the present invention, the efficacy-enhancing agent composition for an agricultural chemical (including a spray prepared from the efficacy-enhancing agent composition and water) and an agricultural chemical ingredient (including a spray preparation from the agricultural chemical ingredient and water) or the agricultural chemical composition (including a spray preparation from the agricultural chemical composition) is preferably contacted with a part of a plant where a water contact angle is 50 to 180 degrees such as a leaf and a stem by dropping or spraying or the like. In general, the surface of a plant is covered with epicuticular wax, cuticular wax, cutin, and the like, and has hydrophobic characteristics. A sprayed solution of an agricultural chemical such as a herbicide, pesticide, or bactericide in water on a plant is accordingly repelled by the hydrophobic surface and cannot wet the plant, resulting in a problematic reduction of effects of the agricultural chemical. The present invention can achieve high effects for efficacy-enhancing of an agricultural chemical by spraying the efficacy-enhancing agent composition for an agricultural chemical and an agricultural chemical ingredient or the agricultural chemical composition of the present invention to a hydrophobic part of a plant to contact or attach them.

A water contact angle is an indicator of hydrophobicity of the surface of a plant. For achieving higher effects for efficacy-enhancing an agricultural chemical of the present invention, a plant preferably has a water contact angle of 50 to 180 degrees, more preferably 70 to 180 degrees, and even more preferably 90 to 180 degrees. The water contact angle is determined by dropping 5 µL of water on the surface of a plant to treat (e.g., the surface of a third leaf), and 10 seconds after, taking a photo of the state of the drop from the side with a microscope, and analyzing an image to calculate a contact angle between the surface and the drop.

Typical plants having a part exhibiting a water contact angle within the range include, but not limited to, those described below. Examples of the weed include Bermuda glass (*Cynodon dactylon*), Egyptian crowfoot grass (*Dactyloctenium aegyptium*), jungle rice (*Echinochloa colona*), cockspur grass (*Echinochloa crus-galli*), Indian goosegrass (*Eleusine indica*), southern crabgrass (*Digitaria ciliaris*), blady grass (*Imperata cylindrica*), southern cut grass (*Leersia hexandra*), Chinese sprangletop (*Leptochloa chinensis*), torpedograss (*Panicum repens*), Napier grass (*Pennisetum purpureum*), itchgrass (*Rottboellia exaltata*), cattail grass (*Setaria pumila* ssp. *pallidefusca*), variable flatsedge (*Cyperus difformis*), rice flatsedge (*Cyperus iria*), purple nutsedge (*Cyperus rotundus*), umbrella sedge (*Fuirena ciliaris*), Indian jointvetch (*Aeschynomene indica*), flossflower (*Ageratum houstonianum*), sessile joyweed (*Alternanthera sessilis*), redroot amaranth (*Amaranthus retroflexus*), Benghal dayflower (*Commelina benghalensis*), creeping spiderwort (*Commelina diffusa. Burm*, f.), common water hyacinth (*Eichhornia crassipes*), asthma weed (*Euphorbia pilulifera*), Indian heliotrope (*Heliotropium indicum*), chan (*Hyptis suaveolens*), nardoo (*Marsilea crenata C. Presl*), sensitive plant (*Mimosa pudica*), oval-leafed pondweed (*Monochoria vaginalis* var. *plantaginea*), verdolaga (*Portulaca oleracea*), coat buttons (*Tridax procumbens*), velvetleaf (*Abutilon theophrasti*), and field horsetail (*Equisetum arvense*). Preferred weeds on which better effects for efficacy-enhancing an agricultural chemical of the present invention are achieved include Bermuda glass, jungle rice, cockspur grass, Indian goosegrass, southern crabgrass, blady grass, southern cut grass, Chinese sprangletop, torpedograss, cattail grass, Indian jointvetch, nardoo, sensitive plant, velvetleaf, and field horsetail, and more preferred weeds include Bermuda glass, jungle rice, cockspur grass, Indian goosegrass, southern crabgrass, blady grass, Indian jointvetch, velvetleaf, and field horsetail.

Further, examples of the agricultural product as the subject of the method of the present invention include barley, pea, rice, wheat, cabbage, eddoe, strawberry, melon, eggplant, tomato, leek, rape, soybean, kidney bean, sweet potato, cucumber, napa cabbage, apple, pear, peach, persimmon, and citrus. Among these agricultural products, preferred agricultural products on which better effects for efficacy-enhancing an agricultural chemical of the present invention are achieved include barley, pea, rice, wheat, cabbage, napa cabbage, eddoe, strawberry, melon, eggplant, tomato, leek, rape, soybean, cucumber, and kidney bean, and more preferred agricultural products include rice, wheat, cabbage, napa cabbage, soybean, leek, kidney bean, and cucumber.

Note that, compounds (A) and (B) can be separated even from the efficacy-enhancing agent composition or the agricultural chemical composition prepared, and detected with a FID detector. For example, the presence or absence of compounds (A) and (B) in the efficacy-enhancing agent composition for an agricultural chemical or the agricultural chemical composition can be quantitatively determined by diluting the composition in an adequate medium such as ethanol and measuring a dilution under the following conditions.

Apparatus: gas chromatography analysis system (Agilent Technologies 6850 Series II)
Column: DB5 ((5%-Phenyl)-Methylpolysiloxane)
Column size: 12 m by 200 μm by 0.33 μm,
Helium gas flow rate: 1.0 mL/min, pressure: 85.0 kPa,
Column temperature conditions (initial temperature: 60° C., holding for 2 min→elevating at 10° C./min→300° C., holding for 14 min)

EXAMPLES

The following Examples demonstrate the present invention. Examples are intended to illustrate the present invention, and not to limit the present invention.

Example 1 and Comparative Example 1

Tables 1 and 2 show compounds (A) and (B) and comparative compounds used in the following Examples and Comparative Examples.

Compounds in Tables 1 and 2 were used in combinations shown in Tables 3 and 4 to prepare efficacy-enhancing agent compositions as shown in Tables 3 and 4 [having compounds shown in Tables 1 and 2 at 100% by weight]. These efficacy-enhancing agent compositions were subjected to a test of wetting and spreading performances, a herbicidal test, an insecticidal test, a miticidal test, and a bactericidal test according to the following methods. All compounds in Tables 1 and 2 excluding compounds B'-3 and B'-4 in Table 2 were products available from Kao Corporation. Compounds B'-3 and B'-4 in Table 2 were products available from Wako Pure Chemical Industries, Ltd. It is noted that, in Tables 3 and 4, compounds not corresponding to the compound (A) or (B) are shown in respective columns for convenience.

[Test of Wetting and Spreading Performances]

Cockspur grass (*Echinochloa crus-galli*) was selected as a test species. Plants of Cockspur grass were cultivated in 12 cm pots for the test. Individuals having eighth leaves were used to conduct the test. Each test liquid of the efficacy-enhancing agent compositions (without an agricultural chemical) was prepared by mixing with water such that concentrations of compounds (A) and (B) in the test liquid were equal to those in a corresponding agricultural chemical spray liquid shown in Tables 3 and 4. On the center of a fifth leaf taken from a plant of cockspur grass, 5 μL of a test liquid was dropped. As a complement data, a measured contact angle between a leaf of cockspur grass and water was 130 degrees. One minute after dropping, the drop was measured about its major and minor axes with a caliper to calculate a surface area covered with the drop regarded as a rectangle. The surface area was used to evaluate properties of the drop to wet and spread on a hydrophobic leaf. The measurement was repeated five times. From results shown in Tables 3 and 4, efficacy-enhancing agent compositions of the present invention were confirmed to have drastically improved wetting and spreading performances.

[Herbicidal Test]

Plants of Cockspur grass were cultivated in 12 cm pots for the test. Individuals having about 18 cm height were used to conduct the test. Each agricultural chemical spray liquid (agricultural chemical composition) was prepared by mixing 1 L of water with 4.8 g of Roundup liquid (herbicide available from Nissan Chemical Industries, Ltd., effective ingredient: 41% by weight in the form of glyphosate isopropylamine salt) and an efficacy-enhancing agent composition [compounds (A) and (B)] in amounts to meet concentrations of the efficacy-enhancing agent composition in spraying as shown in Table 3 or 4. An agricultural chemical spray liquid was applied over the plant by spraying onto leaves, and evaluated for a herbicidal activity. As a complement data, a measured contact angle between a leaf of cockspur grass and water was 130 degrees. For evaluating a herbicidal activity, 14 days after from spraying, an aerial part of the plant was weighed and used to calculate a herbicidal rate according to the following equation, based on a weight of a fresh aerial part of a plant in an untreated area. The higher herbicidal rate refers to the higher agricultural chemical activity (herbicidal activity). In the test, the "untreated area" refers to an area in which a diluted mixture of the agricultural chemical and an efficacy-enhancing agent composition (agricultural chemical spray liquid) were not sprayed (the same applied to other tests).

herbicidal rate (%)=[(weight of an aerial part in an untreated area)−(weight of an aerial part in a treated area)]/(weight of an aerial part in an untreated area)×100

From results shown in Tables 3 and 4, agricultural chemical compositions of the present invention were confirmed to enhance the agricultural chemical activity.

[Insecticidal Test]

Plants of rice were cultivated in 12 cm pots to a height of 15 cm. 10 imagoes of Unka 3 to 5 days old from emergence were released per plant of rice three times and allowed to grow. Each agricultural chemical spray liquid (agricultural chemical composition) was prepared by mixing 1 L of water with 0.3 g of Sumithion emulsion (pesticide available from Sumitomo Chemical Co., Ltd., effective ingredient; 50% by weight fenitrothion) and an efficacy-enhancing agent composition [compounds (A) and (B)] in amounts to meet such concentrations of the efficacy-enhancing agent composition in spraying as shown in Table 3 or 4. An agricultural chemical spray liquid was applied in an amount shown in Table 3 or 4 over the plant of rice infested with Unka by spraying onto leaves. As a complement data, a measured contact angle between a leaf of rice and water was 135 degrees. Plants were dried in the air and covered with a woven metal cylinder for 3 days. Then, the number of survival insects was counted and used to calculate an insecticidal rate according to the following equation. The higher insecticidal rate refers to the higher agricultural chemical activity (insecticidal activity).

insecticidal rate (%)=[(the number of survival insects in an untreated area)−(the number of survival insects in a treated area)]/(the number of survival insects in an untreated area)×100

From results shown in Tables 3 and 4, agricultural chemical compositions of the present invention were confirmed to enhance the insecticidal activity.

[Miticidal Test]

Plants of kidney bean were cultivated in 12 cm pots to a stage of five leaves. 30 individuals of *Tetranychus kanzawai* were released per plant three times. Each agricultural chemical spray liquid (agricultural chemical composition) was prepared by mixing 1 L of water with 0.3 g of Nissorun wettable powder (miticide available from Nippon Soda Co., Ltd., effective ingredient: 10% by weight hexythiazox) and an efficacy-enhancing agent composition [compounds (A) and (B)] in such amount as that a concentration of the efficacy-enhancing agent composition in spraying was as shown in Table 3 or 4. An agricultural chemical spray liquid was applied in an amount shown in Table 3 or 4 over the plant of kidney bean by spraying onto leaves. As a complement data, a measured contact angle between a leaf of kidney bean and water was 100 degrees. Plants were dried in the air and covered with a woven metal cylinder for 3 days. Then, the number of survival mites was counted and used to calculate a miticidal rate according to the following equation. The higher miticidal rate refers to the higher agricultural chemical activity (miticidal activity).

miticidal rate (%)=[(the number of survival mites in an untreated area)−(the number of survival mites in a treated area)]/(the number of survival mites in an untreated area)×100

From results shown in Tables 3 and 4, agricultural chemical compositions of the present invention were confirmed to enhance the miticidal activity.

[Bactericidal Test]

Plants of cucumber were cultivated in 12 cm pots to a stage of three leaves. To these plants, a suspension of spores (at a concentration of $10^7$ spores/mL) of cucumber gray mold-causing fungus (*Botrytis cinerea*) resistant to bactericides was sprayed in an amount of 50 mL/10a. Plants were allowed to stand at 25° C. under 90% relative humidity to be infected by the fungi. Three days after from the infection, each agricultural chemical spray liquid (agricultural chemical composition) was prepared by mixing 1 L of water with 0.5 g of Benlate wettable powder (bactericide available from Sumitomo Chemical Co., Ltd., effective ingredient: 50% by weight benomyl) and an efficacy-enhancing agent composition [compounds (A) and (B)] in such amount as that a concentration of the efficacy-enhancing agent composition in spraying was as shown in Table 3 and 4, and applied in an amount shown in Table 3 and 4 over the plant of cucumber by spraying onto leaves. As a complement data, a measured contact angle between a leaf of cucumber and water was 90 degrees. Pots were allowed to stand at 25° C. under 85% relative humidity for a week. Then, the number of lesions was counted and used to calculate a controlling value according to the following equation. The higher controlling value refers to the higher agricultural chemical activity (bactericidal activity).

controlling value (%)={1−(the number of lesions in a treated area/the number of lesions in an untreated area)}×100

From results shown in Tables 3 and 4, agricultural chemical compositions of the present invention were confirmed to enhance the bactericidal activity.

TABLE 1

| | | | Meaning in formula(A1) | | |
|---|---|---|---|---|---|
| | symbol | Compound | $R^{1a}$ | l | $R^{2a}$ |
| Compound (A) | A-1 | Polyoxyethylene(4)lauryl ether | Lauryl group | 4 | Hydrogen atom |
| | A-2 | Polyoxyethylene(5)lauryl ether | Lauryl group | 5 | Hydrogen atom |
| | A-3 | Polyoxyethylene(6)lauryl ether | Lauryl group | 6 | Hydrogen atom |
| | A-4 | Polyoxyethylene(9)lauryl ether | Lauryl group | 9 | Hydrogen atom |
| | A-5 | Polyoxyethylene(21)lauryl ether | Lauryl group | 21 | Hydrogen atom |
| | A-6 | Polyoxyethylene(40)lauryl ether | Lauryl group | 40 | Hydrogen atom |
| | A-7 | Polyoxyethylene(7)cetyl ether | Cetyl group | 7 | Hydrogen atom |
| | A-8 | Polyoxyethylene(13)cetyl ether | Cetyl group | 13 | Hydrogen atom |
| | A-9 | Polyoxyethylene(5) sec-alkyl($C_{12}$) ether (secondary alcohol ether) | Secondary alkyl group having 12 carbon atoms | 5 | Hydrogen atom |
| | A-10 | Polyoxyethylene(7) sec-alkyl($C_{12}$) ether (secondary alcohol ether) | Secondary alkyl group having 12 carbon atoms | 7 | Hydrogen atom |
| | A-11 | Polyoxyethylene(9)sec-alkyl($C_{12}$) ether (secondary alcohol ether) | Secondary alkyl group having 12 carbon atoms | 9 | Hydrogen atom |
| Comparative compound | A'-1 | Polyoxyethylene(2)lauryl ether | Lauryl group | 2 | Hydrogen atom |
| | A'-2 | Polyoxyethylene(47) lauryl ether | Lauryl group | 47 | Hydrogen atom |
| | A'-3 | Polyoxyethylene(8)oleyl ether | Oleyl group | 8 | Hydrogen atom |
| | A'-4 | Polyoxyethylene(6)stearyl ether | Stearyl group | 6 | Hydrogen atom |

*The number in parentheses represents an average mole number of oxyethylene groups added (the same applies to the following Tables)

TABLE 2

| | | | Structure in the formula(B1) | | | |
|---|---|---|---|---|---|---|
| | symbol | Compound | $R^{1b}$ | m | n | m/(m + n) | $R^{2b}$ |
| Compound(B) | B-1 | Polyoxypropylene(3) hexyl ether | Hexyl group | 3 | 0 | 1 | Hydrogen atom |
| | B-2 | Polyoxypropylene(3) octyl ether | Octyl group | 3 | 0 | 1 | Hydrogen atom |
| | B-3 | Polyoxypropylene(7) octyl ether | Octyl group | 7 | 0 | 1 | Hydrogen atom |
| | B-4 | Polyoxypropylene(10)octyl ether | Octyl group | 10 | 0 | 1 | Hydrogen atom |

TABLE 2-continued

|  |  |  |  | Structure in the formula(B1) | | | |
|---|---|---|---|---|---|---|---|
|  | symbol | Compound | $R^{1b}$ | m | n | m/(m + n) | $R^{2b}$ |
|  | B-5 | Polyoxypropylene(15)octyl ether | Octyl group | 15 | 0 | 1 | Hydrogen atom |
|  | B-6 | Polyoxypropylene(20)octyl ether | Octyl group | 20 | 0 | 1 | Hydrogen atom |
|  | B-7 | Polyoxypropylene(3) decyl ether | Decyl group | 3 | 0 | 1 | Hydrogen atom |
|  | B-8 | Polyoxypropylene(3) lauryl ether | Lauryl group | 3 | 0 | 1 | Hydrogen atom |
|  | B-9 | Polyoxypropylene(6)polyoxyethylene(3)-2-ethylhexyl ether | 2-ethylhexyl group | 6 | 3 | 0.67 | Hydrogen atom |
| Comparative compound | B'-1 | Polyoxypropylene(3) butyl ether | Butyl group | 3 | 0 | 1 | Hydrogen atom |
|  | B'-2 | Polyoxypropylene(30) octyl ether | Octyl group | 30 | 0 | 1 | Hydrogen atom |
|  | B'-3 | Polypropylene glycol (weight average molecular weight: 300) | Hydrogen atom | 5 | 0 | 1 | Hydrogen atom |
|  | B'-4 | Polyethylene glycol (weight average molecular weight: 1000) | Hydrogen atom | 0 | 25 | 0 | Hydrogen atom |

TABLE 3

|  |  |  |  |  | Agrochemical sprayed liquid | | Results of evaluation | | | | |
|---|---|---|---|---|---|---|---|---|---|---|---|
|  |  | Compound (A) | Compound (B) | Weight ratio of (A)/(B) | amount of spraying | Concentration of (A) + (B) (ppm) | Wetting and spreading performances ($mm^2$) | Herbicidal rate (%) | Insecticidal test (%) | Miticidal rate (%) | Controlling value (%) |
| Example | 1-1 | A-1 | B-2 | 1 | 25L/10a | 1000 | 221 | 83 | 81 | 80 | 76 |
|  | 1-2 | A-2 | B-2 | 1 | 25L/10a | 1000 | 316 | 90 | 85 | 84 | 82 |
|  | 1-3 | A-3 | B-2 | 1 | 25L/10a | 1000 | 412 | 96 | 90 | 92 | 91 |
|  | 1-4 | A-4 | B-2 | 1 | 25L/10a | 1000 | 386 | 95 | 89 | 91 | 90 |
|  | 1-5 | A-5 | B-2 | 1 | 25L/10a | 1000 | 329 | 90 | 84 | 84 | 83 |
|  | 1-6 | A-6 | B-2 | 1 | 25L/10a | 1000 | 166 | 75 | 72 | 72 | 70 |
|  | 1-7 | A-7 | B-2 | 1 | 25L/10a | 1000 | 230 | 85 | 83 | 82 | 79 |
|  | 1-8 | A-8 | B-2 | 1 | 25L/10a | 1000 | 195 | 80 | 77 | 77 | 74 |
|  | 1-9 | A-9 | B-2 | 1 | 25L/10a | 1000 | 213 | 82 | 80 | 78 | 75 |
|  | 1-10 | A-10 | B-2 | 1 | 25L/10a | 1000 | 330 | 92 | 87 | 86 | 85 |
|  | 1-11 | A-11 | B-2 | 1 | 25L/10a | 1000 | 374 | 95 | 88 | 90 | 89 |
|  | 1-12 | A-3 | B-1 | 1 | 25L/10a | 1000 | 218 | 82 | 80 | 78 | 75 |
|  | 1-13 | A-3 | B-3 | 1 | 25L/10a | 1000 | 415 | 96 | 93 | 94 | 93 |
|  | 1-14 | A-3 | B-4 | 1 | 25L/10a | 1000 | 421 | 98 | 94 | 95 | 94 |
|  | 1-15 | A-3 | B-5 | 1 | 25L/10a | 1000 | 416 | 97 | 93 | 93 | 92 |
|  | 1-16 | A-3 | B-6 | 1 | 25L/10a | 1000 | 256 | 84 | 82 | 81 | 78 |
|  | 1-17 | A-3 | B-7 | 1 | 25L/10a | 1000 | 212 | 83 | 81 | 79 | 75 |
|  | 1-18 | A-3 | B-8 | 1 | 25L/10a | 1000 | 180 | 77 | 76 | 73 | 71 |
|  | 1-19 | A-3 | B-9 | 1 | 25L/10a | 1000 | 333 | 92 | 86 | 89 | 87 |
|  | 1-20 | A-3 | B-2 | 0.11 | 25L/10a | 1000 | 138 | 72 | 71 | 71 | 70 |
|  | 1-21 | A-3 | B-2 | 0.33 | 25L/10a | 1000 | 234 | 85 | 83 | 82 | 74 |
|  | 1-22 | A-3 | B-2 | 3 | 25L/10a | 1000 | 266 | 87 | 86 | 85 | 77 |
|  | 1-23 | A-3 | B-2 | 9 | 25L/10a | 1000 | 169 | 74 | 73 | 72 | 71 |
|  | 1-24 | A-3 | B-2 | 1 | 25L/10a | 10000 | 301 | 88 | 84 | 83 | 82 |
|  | 1-25 | A-3 | B-2 | 1 | 25L/10a | 5000 | 384 | 95 | 92 | 93 | 91 |
|  | 1-26 | A-3 | B-2 | 1 | 25L/10a | 2000 | 412 | 96 | 93 | 94 | 93 |
|  | 1-27 | A-3 | B-2 | 1 | 25L/10a | 600 | 259 | 87 | 84 | 82 | 80 |
|  | 1-28 | A-3 | B-2 | 1 | 25L/10a | 300 | 180 | 78 | 76 | 75 | 73 |
|  | 1-29 | A-3 | B-2 | 1 | 25L/10a | 100 | 154 | 73 | 72 | 70 | 70 |

TABLE 4

|  |  |  |  |  | Agrochemical sprayed liquid | | Results of evaluation | | | | |
|---|---|---|---|---|---|---|---|---|---|---|---|
|  |  | Compound (A) | Compound (B) | Weight ratio of (A)/(B) | amount of spraying | Concentration of (A) + (B) (ppm) | Wetting and spreading performances ($mm^2$) | Herbicidal rate (%) | Insecticidal test (%) | Miticidal rate (%) | Controlling value (%) |
| Example | 1-30 | A-3 | B-2 | 1 | 7L/10a | 1000 | 416 | 97 | 95 | 94 | 93 |
|  | 1-31 | A-3 | B-2 | 1 | 50L/10a | 1000 | 380 | 95 | 88 | 90 | 89 |
|  | 1-32 | A-3 | B-2 | 1 | 100L/10a | 1000 | 340 | 93 | 87 | 88 | 88 |

TABLE 4-continued

|  |  | Compound (A) | Compound (B) | Weight ratio of (A)/(B) | Agrochemical sprayed liquid | | Results of evaluation | | | | |
|---|---|---|---|---|---|---|---|---|---|---|---|
|  |  |  |  |  | amount of spraying | Concentration of (A) + (B) (ppm) | Wetting and spreading performances (mm$^2$) | Herbicidal rate (%) | Insecticidal test (%) | Miticidal rate (%) | Controlling value (%) |
|  | 1-33 | A-3 | B-2 | 1 | 200L/10a | 1000 | 319 | 90 | 85 | 86 | 86 |
| Comparative example | 1-1 | — | — | — | 25L/10a | 0 | 4 | 43 | 41 | 44 | 42 |
|  | 1-2 | A-1 | — | — | 25L/10a | 1000 | 8 | 46 | 44 | 47 | 45 |
|  | 1-3 | A-3 | — | — | 25L/10a | 1000 | 20 | 50 | 48 | 51 | 48 |
|  | 1-4 | A-5 | — | — | 25L/10a | 1000 | 11 | 47 | 45 | 48 | 46 |
|  | 1-5 | A-7 | — | — | 25L/10a | 1000 | 10 | 46 | 45 | 46 | 46 |
|  | 1-6 | A-9 | — | — | 25L/10a | 1000 | 18 | 49 | 47 | 50 | 47 |
|  | 1-7 | — | B-2 | 0 | 25L/10a | 1000 | 13 | 45 | 44 | 45 | 43 |
|  | 1-8 | — | B-4 | 0 | 25L/10a | 1000 | 6 | 44 | 43 | 45 | 43 |
|  | 1-9 | — | B-6 | 0 | 25L/10a | 1000 | 5 | 44 | 43 | 45 | 42 |
|  | 1-10 | — | B-9 | 0 | 25L/10a | 1000 | 19 | 44 | 43 | 45 | 43 |
|  | 1-11 | A'-1 | B-2 | 1 | 25L/10a | 1000 | 13 | 57 | 55 | 56 | 54 |
|  | 1-12 | A'-2 | B-2 | 1 | 25L/10a | 1000 | 14 | 54 | 51 | 55 | 52 |
|  | 1-13 | A'-3 | B-2 | 1 | 25L/10a | 1000 | 13 | 51 | 48 | 52 | 49 |
|  | 1-14 | A'-4 | B-2 | 1 | 25L/10a | 1000 | 13 | 52 | 49 | 53 | 50 |
|  | 1-15 | A-3 | B'-1 | 1 | 25L/10a | 1000 | 27 | 53 | 51 | 52 | 49 |
|  | 1-16 | A-3 | B'-2 | 1 | 25L/10a | 1000 | 35 | 54 | 53 | 54 | 52 |
|  | 1-17 | A-3 | B'-3 | 1 | 25L/10a | 1000 | 23 | 51 | 49 | 52 | 49 |
|  | 1-18 | A-3 | B'-4 | 1 | 25L/10a | 1000 | 20 | 51 | 49 | 51 | 49 |

Example 2 and Comparative Example 2

Table 5 shows compounds (A) and comparative compounds used in the following Examples and Comparative Examples. Compounds (A) in Table 5 (some compounds (A) shown in Table 1 in Example 1 were also used) and compounds (B) in Table 2 in Example 1 were used in combinations shown in Table 6 to prepare efficacy-enhancing agent compositions of agricultural chemical activity as shown in Table 6 [some containing compounds in Tables 5 and 2 at 100%, others containing compounds in Tables 5 and 2 and a solvent]. These efficacy-enhancing agent compositions were subjected to the test of wetting and spreading performances, the herbicidal test, the insecticidal test, the miticidal test, and the bactericidal test in the same way as in Example 1. Results are shown in Table 6. It is noted that, in Table 6, a compound not corresponding to the compound (A) nor (B) was shown in either column for convenience. As shown in Table 6, Examples 2-17, 2-18, and 2-19 used 10% by weight of water, 10% by weight of ethyl lactate, and 10% by weight of diethylene glycol, respectively, as a solvent.

From results shown in Table 6, agricultural chemical compositions of the present invention were confirmed to have drastically improved wetting and spreading performances and to enhance the herbicidal, the insecticidal, the miticidal, and the bactericidal activities.

TABLE 5

|  | Symbol | Compound |
|---|---|---|
| Compound (A) | A-12 | Polyoxyethylene(12) monolauric acid ester |
|  | A-13 | Polyoxyethylene(6) sorbitane monolauric acid ester |
|  | A-14 | Polyoxyethylene(20) sorbitane monolauric ester |
|  | A-15 | Diglycerol monolaurate |
|  | A-16 | Diglycerol monocaprate |
|  | A-17 | Glycerol monocaprate |
|  | A-18 | Decyl glucoside [p = 1.3 in the formula(A5)] |
|  | A-19 | Lauryl glucoside [p = 4.6 in the for,mula(A5)] |
| Comparative compound | A'-5 | Polyoxyethylene(9) monooleic acid ester |
|  | A'-6 | Polyoxyethylene(6) sorbitane monooleic acid ester |
|  | A'-7 | Monooleic diglycerine |
|  | A'-8 | Polyoxyethylene(5) polyoxypropylene(35) block copolymer |
|  | A'-9 | Sorbitane monooleic acid ester |
|  | B'-5 | Palmityl alcohol |
|  | B'-6 | Dipropylene glycol dimethyl ether |
|  | B'-7 | Polyoxypropylene(3) palmityl ether |

TABLE 6

| | | Compound (A) | Compound (B) | (A)/(B) weight ratio | Agrochemical sprayed liquid amount of spraying | Concentration of (A) + (B) (ppm) | Wetting and spreading performances (mm²) | Result of evaluation Herbicidal rate (%) | Insecticidal test (%) | Miticidal rate (%) | Controlling value (%) | Solvent and its concentration in efficacy-enhancing composition for agriculture |
|---|---|---|---|---|---|---|---|---|---|---|---|---|
| Example | 2-1 | A-12 | B-2 | 1 | 25L/10a | 1000 | 213 | 83 | 84 | 83 | 82 | — |
| | 2-2 | A-13 | B-2 | 1 | 25L/10a | 1000 | 124 | 76 | 77 | 77 | 77 | — |
| | 2-3 | A-14 | B-2 | 1 | 25L/10a | 1000 | 85 | 72 | 71 | 70 | 70 | — |
| | 2-4 | A-15 | B-2 | 1 | 25L/10a | 1000 | 246 | 86 | 85 | 85 | 86 | — |
| | 2-5 | A-16 | B-2 | 1 | 25L/10a | 1000 | 135 | 77 | 78 | 77 | 77 | — |
| | 2-6 | A-17 | B-2 | 1 | 25L/10a | 1000 | 74 | 70 | 71 | 70 | 70 | — |
| | 2-7 | A-18 | B-2 | 1 | 25L/10a | 1000 | 238 | 85 | 85 | 83 | 84 | — |
| | 2-8 | A-19 | B-2 | 1 | 25L/10a | 1000 | 312 | 92 | 91 | 92 | 91 | — |
| | 2-9 | A-19 | B-1 | 1 | 25L/10a | 1000 | 239 | 85 | 85 | 84 | 85 | — |
| | 2-10 | A-19 | B-3 | 1 | 25L/10a | 1000 | 324 | 93 | 92 | 93 | 92 | — |
| | 2-11 | A-19 | B-4 | 1 | 25L/10a | 1000 | 326 | 93 | 93 | 93 | 93 | — |
| | 2-12 | A-19 | B-5 | 1 | 25L/10a | 1000 | 243 | 85 | 86 | 86 | 85 | — |
| | 2-13 | A-19 | B-6 | 1 | 25L/10a | 1000 | 148 | 78 | 78 | 78 | 77 | — |
| | 2-14 | A-19 | B-7 | 1 | 25L/10a | 1000 | 255 | 87 | 86 | 87 | 88 | — |
| | 2-15 | A-19 | B-8 | 1 | 25L/10a | 1000 | 211 | 82 | 82 | 81 | 82 | — |
| | 2-16 | A-19 | B-9 | 1 | 25L/10a | 1000 | 308 | 91 | 91 | 91 | 90 | — |
| | 2-17 | A-3 | B-2 | 1 | 25L/10a | 1000 | 420 | 96 | 92 | 93 | 92 | Water 10% by weight |
| | 2-18 | A-3 | B-2 | 1 | 25L/10a | 1000 | 422 | 97 | 93 | 94 | 92 | Ethyl lactate 10% by weight |
| | 2-19 | A-3 | B-2 | 1 | 25L/10a | 1000 | 435 | 98 | 94 | 95 | 94 | Diethylene glycol 10% by weight |

TABLE 6-continued

| | | Compound (A) | Compound (B) | (A)/(B) weight ratio | Agrochemical sprayed liquid amount of spraying | Concentration of (A) + (B) (ppm) | Wetting and spreading performances (mm²) | Result of evaluation Herbicidal rate (%) | Insecticidal test (%) | Miticidal rate (%) | Controlling value (%) | Solvent and its concentration in efficacy-enhancing composition for agriculture |
|---|---|---|---|---|---|---|---|---|---|---|---|---|
| Comparative example | 2-1 | A-12 | — | — | 25L/10a | 1000 | 7 | 44 | 43 | 45 | 43 | — |
| | 2-2 | A-13 | — | — | 25L/10a | 1000 | 5 | 43 | 41 | 44 | 43 | — |
| | 2-3 | A-14 | — | — | 25L/10a | 1000 | 5 | 43 | 42 | 43 | 43 | — |
| | 2-4 | A-15 | — | — | 25L/10a | 1000 | 6 | 44 | 43 | 44 | 43 | — |
| | 2-5 | A-16 | — | — | 25L/10a | 1000 | 5 | 43 | 43 | 43 | 43 | — |
| | 2-6 | A-17 | — | — | 25L/10a | 1000 | 5 | 42 | 42 | 43 | 43 | — |
| | 2-7 | A-18 | — | — | 25L/10a | 1000 | 6 | 44 | 43 | 44 | 43 | — |
| | 2-8 | A-19 | — | — | 25L/10a | 1000 | 6 | 44 | 44 | 45 | 44 | — |
| | 2-9 | A-5 | B-2 | 1 | 25L/10a | 1000 | 12 | 46 | 46 | 47 | 46 | — |
| | 2-10 | A-6 | B-2 | 1 | 25L/10a | 1000 | 14 | 48 | 47 | 48 | 47 | — |
| | 2-11 | A-7 | B-2 | 1 | 25L/10a | 1000 | 13 | 47 | 47 | 47 | 47 | — |
| | 2-12 | A-19 | B-1 | 1 | 25L/10a | 1000 | 21 | 51 | 50 | 51 | 51 | — |
| | 2-13 | A-19 | B-2 | 1 | 25L/10a | 1000 | 24 | 53 | 53 | 52 | 53 | — |
| | 2-14 | A-19 | B-3 | 1 | 25L/10a | 1000 | 23 | 51 | 49 | 52 | 49 | — |
| | 2-15 | A-19 | B-4 | 1 | 25L/10a | 1000 | 20 | 51 | 49 | 51 | 49 | — |
| | 2-16 | A-8 | B-2 | 1 | 25L/10a | 1000 | 4 | 43 | 42 | 44 | 43 | — |
| | 2-17 | A-9 | B-2 | 1 | 25L/10a | 1000 | 5 | 45 | 43 | 45 | 44 | — |
| | 2-18 | A-12 | B-5 | 1 | 25L/10a | 1000 | 7 | 45 | 44 | 45 | 44 | — |
| | 2-19 | A-12 | B-6 | 1 | 25L/10a | 1000 | 4 | 43 | 41 | 43 | 43 | — |
| | 2-20 | Combination of A-3 and A-12 at 1:1 (weight | — | — | 25L/10a | 1000 | 7 | 45 | 44 | 45 | 44 | — |
| | 2-21 | A-12 | B-7 | 1 | 25L/10a | 1000 | 14 | 48 | 48 | 48 | 47 | — |

Example 3 and Comparative Example 3

Tables 7 and 8 show compounds (A) and (B2) and comparative compounds used in the following Examples and Comparative Examples.

Compounds in Tables 7 and 8 were used in combinations shown in Tables 9 and 10 to prepare efficacy-enhancing agent compositions as shown in Tables 9 and 10 [some containing compounds in Tables 7 and 8 at 100%, others containing compounds in Tables 7 and 8 and a solvent]. These efficacy-enhancing agent compositions were subjected to a test of wetting and spreading performances, a herbicidal test, an insecticidal test, a miticidal test, and a bactericidal test according to the following methods. All compounds in Tables 7 and 8 excluding compounds A-2-11, A-2-12, and A'-2-7 in Table 7 were products available from Kao Corporation. Compounds A-2-11, A-2-12, and A'-2-7 in Table 7 were products available from Taiyo Kagaku Co., Ltd. It is noted that, in Table 10, a compound not corresponding to the compound (A) nor (B) was shown in either column for convenience. As shown in Table 10, Examples 1-2-33, 1-2-34, and 1-2-35 used 10% by weight of water, 10% by weight of ethyl lactate, and 10% by weight of diethylene glycol, respectively, as a solvent.

TABLE 8

| | symbol | Compound |
|---|---|---|
| Compound (B) | B-2-1 | Octyl alcohol [$R^{2a}$ = octyl group in the formula(B1)] |
| | B-2-2 | Decyl alcohol [$R^{2a}$ = decyl group in the formula(B1)] |
| | B-2-3 | Lauryl alcohol [$R^{2a}$ = lauryl group in the formula(B1)] |
| | B-2-4 | Myristyl alcohol [$R^{2a}$ = myristyl group in the formula(B1)] |
| Comparative compound | B'-2-1 | Ethanol [$R^{2a}$ = ethyl group in the formula(B1)] |
| | B'-2-2 | Butanol [$R^{2a}$ = butyl group in the formula(B1)] |
| | B'-2-3 | Palmityl alcohol [$R^{2a}$ = palmityl group in the formula(B1)] |
| | B'-2-4 | Stearyl alcohol [$R^{2a}$ = stearyl group in the formula(B1)] |

TABLE 7

| Compound group | | symbol | Compound |
|---|---|---|---|
| Compound (A) | (A1) | A-2-1 | Polyoxyethylene(4) lauryl ether [in the formula(A1), $R^{1a}$ = lauric group, l = 4, $R^{2a}$ = hydrogen atom] |
| | | A-2-2 | Polyoxyethylene(6) lauryl ether [in the formula(A1), $R^{1a}$ = lauryl group, l = 6, $R^{2a}$ = hydrogen atom] |
| | | A-2-3 | Polyoxyethylene(9) lauryl ether [in the formula(A1), $R^{1a}$ = lauryl group, l = 9, $R^{2a}$ = hydrogen atom] |
| | | A-2-4 | Polyoxyethylene(21) lauryl ether [in the formula(A1), $R^{1a}$ = lauryl group, l = 21, $R^{2a}$ = hydrogen atom] |
| | | A-2-5 | Polyoxyethylene(40) lauryl ether [in the formula(A1), $R^{1a}$ = lauryl group, l = 40, $R^{2a}$ = hydrogen atom] |
| | | A-2-6 | Polyoxyethylene(13) cetyl ether [in the formula(A1), $R^{1a}$ = cetyl group, l = 13, $R^{2a}$ = hydrogen atom] |
| | | A-2-7 | Polyoxyethylene(7) sec-alkyl($C_{12}$) ether (secondary alcohol ether) [in the formula(A1), $R^{1a}$ = secondary alkyl group having 12 carbon atoms, l = 7, $R^{2a}$ = hydrogen atom] |
| | (A2) | A-2-8 | Polyoxyethylene(12) lauric acid monoester |
| | (A3) | A-2-9 | Polyoxyethylene(6) sorbitane monolauric acid ester |
| | | A-2-10 | Polyoxyethylene(20) sorbitan monolauric acid ester |
| | (A4) | A-2-11 | Diglycerol monolaurate |
| | | A-2-12 | Diglycerol monocaprylate |
| | | A-2-13 | Glycerol monocaprylate |
| | (A5) | A-2-14 | Decyl glucoside [p = 1.3 in the formula(A5)] |
| | | A-2-15 | Lauryl glucoside [p = 4.6 in the formula(A5)] |
| Comparative compound | — | A'-2-1 | Polyoxyethylene(2) lauryl ether [$R^{1a}$ = lauryl group, l = 2, $R^{2a}$ = hydrogen atom in the formula(A1)] |
| | — | A'-2-2 | Polyoxyethylene(47) lauryl ether [$R^{1a}$ = lauryl group, l = 47, $R^{2a}$ = hydrogen atom in the formula(A1)] |
| | — | A'-2-3 | Polyoxyethylene(8) oleyl ether [$R^{1a}$ = oleyl group, l = 8, $R^{2a}$ = hydrogen atom in the formula(A1)] |
| | — | A'-2-4 | Polyoxyethylene(6) stearyl ether [$R^{1a}$ = stearyl group, l = 6, $R^{2a}$ = hydrogen atom in the formula(A1)] |
| | — | A'-2-5 | Polyoxyethylene(9) oleic acid ester |
| | — | A'-2-6 | Polyoxyethylene(6) sorbitane monooleic acid ester |
| | — | A'-2-7 | Diglycerol monooleate |

*The number in parentheses represents an average mole number of oxyethylene groups added.

TABLE 9

| | | Compound (A) | Compound (B) | Weight ratio of (A)/(B) | Agrochemical spray liquid | | Results of evaluation | | | | |
|---|---|---|---|---|---|---|---|---|---|---|---|
| | | | | | amount of spraying | Concentration of (A) + (B) (ppm) | Wetting and spreading performances | Herb- icidal rate (%) | Insect- icidal rate (%) | Miticidal rate (%) | Controlling value (%) |
| Example | 1-2-1 | A-2-1 | B-2-2 | 1 | 25L/10a | 1000 | 130 | 78 | 79 | 79 | 80 |
| | 1-2-2 | A-2-2 | B-2-2 | 1 | 25L/10a | 1000 | 273 | 92 | 92 | 92 | 93 |
| | 1-2-3 | A-2-3 | B-2-2 | 1 | 25L/10a | 1000 | 320 | 94 | 93 | 94 | 95 |
| | 1-2-4 | A-2-4 | B-2-2 | 1 | 25L/10a | 1000 | 233 | 86 | 86 | 87 | 86 |
| | 1-2-5 | A-2-5 | B-2-2 | 1 | 25L/10a | 1000 | 141 | 79 | 80 | 80 | 80 |
| | 1-2-6 | A-2-6 | B-2-2 | 1 | 25L/10a | 1000 | 130 | 78 | 79 | 79 | 80 |
| | 1-2-7 | A-2-7 | B-2-2 | 1 | 25L/10a | 1000 | 268 | 91 | 91 | 90 | 91 |
| | 1-2-8 | A-2-8 | B-2-2 | 1 | 25L/10a | 1000 | 256 | 90 | 91 | 90 | 90 |
| | 1-2-9 | A-2-9 | B-2-2 | 1 | 25L/10a | 1000 | 131 | 79 | 79 | 79 | 80 |
| | 1-2-10 | A-2-10 | B-2-2 | 1 | 25L/10a | 1000 | 89 | 75 | 75 | 74 | 75 |
| | 1-2-11 | A-2-11 | B-2-2 | 1 | 25L/10a | 1000 | 345 | 95 | 95 | 95 | 95 |
| | 1-2-12 | A-2-12 | B-2-2 | 1 | 25L/10a | 1000 | 186 | 82 | 82 | 81 | 82 |
| | 1-2-13 | A-2-13 | B-2-2 | 1 | 25L/10a | 1000 | 77 | 73 | 73 | 72 | 72 |
| | 1-2-14 | A-2-14 | B-2-2 | 1 | 25L/10a | 1000 | 128 | 78 | 77 | 78 | 78 |
| | 1-2-15 | A-2-15 | B-2-2 | 1 | 25L/10a | 1000 | 165 | 80 | 81 | 80 | 80 |
| | 1-2-16 | A-2-8 | B-2-1 | 1 | 25L/10a | 1000 | 235 | 87 | 86 | 87 | 87 |
| | 1-2-17 | A-2-8 | B-2-3 | 1 | 25L/10a | 1000 | 230 | 85 | 86 | 85 | 85 |
| | 1-2-18 | A-2-8 | B-2-4 | 1 | 25L/10a | 1000 | 132 | 79 | 79 | 78 | 79 |
| | 1-2-19 | A-2-8 | B-2-2 | 0.11 | 25L/10a | 1000 | 86 | 74 | 74 | 74 | 74 |
| | 1-2-20 | A-2-8 | B-2-2 | 0.33 | 25L/10a | 1000 | 164 | 80 | 80 | 79 | 80 |
| | 1-2-21 | A-2-8 | B-2-2 | 3 | 25L/10a | 1000 | 156 | 79 | 79 | 79 | 80 |
| | 1-2-22 | A-2-8 | B-2-2 | 9 | 25L/10a | 1000 | 51 | 70 | 70 | 71 | 70 |
| | 1-2-23 | A-2-8 | B-2-2 | 1 | 25L/10a | 10000 | 516 | 97 | 97 | 96 | 97 |
| | 1-2-24 | A-2-8 | B-2-2 | 1 | 25L/10a | 5000 | 422 | 96 | 96 | 96 | 96 |
| | 1-2-25 | A-2-8 | B-2-2 | 1 | 25L/10a | 2000 | 301 | 94 | 94 | 93 | 93 |
| | 1-2-26 | A-2-8 | B-2-2 | 1 | 25L/10a | 600 | 203 | 83 | 83 | 82 | 83 |
| | 1-2-27 | A-2-8 | B-2-2 | 1 | 25L/10a | 300 | 144 | 79 | 80 | 80 | 80 |
| | 1-2-28 | A-2-8 | B-2-2 | 1 | 25L/10a | 100 | 86 | 74 | 74 | 73 | 74 |

TABLE 10

| | | Compound (A) | Compound (B) | Weight ratio of (A)/(B) | Agrochemical spray liquid amount of spraying | Concentration of (A) + (B) (ppm) | Wetting and spreading performances (mm²) | Results of evaluation Herbicidal rate (%) | Insecticidal rate (%) | Miticidal rate (%) | Controlling value (%) | Solvent and its concentration in efficacy-enhancing composition for agriculture |
|---|---|---|---|---|---|---|---|---|---|---|---|---|
| Example | 1-2-29 | A-2-8 | B-2-2 | 1 | 7L/10a | 1000 | 256 | 93 | 93 | 93 | 93 | — |
| | 1-2-30 | A-2-8 | B-2-2 | 1 | 50L/10a | 1000 | 256 | 88 | 87 | 88 | 88 | — |
| | 1-2-31 | A-2-8 | B-2-2 | 1 | 100L/10a | 1000 | 256 | 82 | 83 | 82 | 82 | — |
| | 1-2-32 | A-2-8 | B-2-2 | 1 | 200L/10a | 1000 | 256 | 76 | 77 | 77 | 76 | — |
| | 1-2-33 | A-2-8 | B-2-2 | 1 | 25L/10a | 1000 | 263 | 91 | 92 | 91 | 92 | Water 10% by weight |
| | 1-2-34 | A-2-8 | B-2-2 | 1 | 25L/10a | 1000 | 267 | 92 | 93 | 92 | 92 | Ethyl lactate 10% by weight |
| | 1-2-35 | A-2-8 | B-2-2 | 1 | 25L/10a | 1000 | 278 | 93 | 94 | 93 | 94 | Diethylene glycol 10% by weight |
| Comparative example | 1-2-1 | — | — | — | 25L/10a | 0 | 4 | 43 | 41 | 44 | 42 | — |
| | 1-2-2 | A-2-2 | — | — | 25L/10a | 1000 | 14 | 47 | 47 | 47 | 47 | — |
| | 1-2-3 | A-2-5 | — | — | 25L/10a | 1000 | 6 | 43 | 42 | 44 | 42 | — |
| | 1-2-4 | A-2-8 | — | — | 25L/10a | 1000 | 7 | 44 | 43 | 45 | 43 | — |
| | 1-2-5 | A-2-9 | — | — | 25L/10a | 1000 | 5 | 43 | 41 | 44 | 43 | — |
| | 1-2-6 | A-2-11 | — | — | 25L/10a | 1000 | 6 | 44 | 43 | 44 | 43 | — |
| | 1-2-7 | A-2-14 | — | — | 25L/10a | 1000 | 6 | 44 | 43 | 44 | 43 | — |
| | 1-2-8 | — | B-2-1 | 0 | 25L/10a | 1000 | 5 | 43 | 41 | 44 | 43 | — |
| | 1-2-9 | — | B-2-2 | 0 | 25L/10a | 1000 | 5 | 43 | 41 | 44 | 43 | — |
| | 1-2-10 | — | B-2-4 | 0 | 25L/10a | 1000 | 5 | 43 | 41 | 44 | 43 | — |
| | 1-2-11 | A'-2-1 | B-2-2 | 1 | 25L/10a | 1000 | 18 | 48 | 48 | 49 | 48 | — |
| | 1-2-12 | A'-2-2 | B-2-2 | 1 | 25L/10a | 1000 | 16 | 47 | 48 | 48 | 47 | — |
| | 1-2-13 | A'-2-3 | B-2-2 | 1 | 25L/10a | 1000 | 16 | 47 | 48 | 48 | 47 | — |
| | 1-2-14 | A'-2-4 | B-2-2 | 1 | 25L/10a | 1000 | 11 | 45 | 45 | 45 | 45 | — |
| | 1-2-11 | A'-2-5 | B-2-2 | 1 | 25L/10a | 1000 | 15 | 47 | 47 | 47 | 47 | — |
| | 1-2-12 | A'-2-6 | B-2-2 | 1 | 25L/10a | 1000 | 12 | 45 | 46 | 45 | 46 | — |
| | 1-2-13 | A'-2-7 | B-2-2 | 1 | 25L/10a | 1000 | 13 | 45 | 46 | 45 | 46 | — |
| | 1-2-15 | A-2-8 | B'-2-1 | 1 | 25L/10a | 1000 | 8 | 44 | 44 | 45 | 44 | — |
| | 1-2-16 | A-2-8 | B'-2-2 | 1 | 25L/10a | 1000 | 8 | 44 | 44 | 45 | 44 | — |
| | 1-2-17 | A-2-8 | B'-2-3 | 1 | 25L/10a | 1000 | 12 | 45 | 46 | 45 | 46 | — |
| | 1-2-18 | A-2-8 | B'-2-4 | 1 | 25L/10a | 1000 | 10 | 45 | 45 | 45 | 45 | — |

The invention claimed is:

1. A method for producing an agricultural product, comprising a step of applying an agricultural chemical composition comprising (A) at least one compound selected from the group consisting of the following (A1) to (A5); (B) at least one compound selected from the group consisting of the following (B1) and (B2); and an agricultural chemical ingredient selected from the group consisting of active ingredients in bactericides, pesticides, miticides, herbicides and plant growth regulators to a subject sensitive to the agricultural chemical ingredient:

(A1): a polyoxyethylene alkyl ether represented by the formula (A1):

$$R^{1a}O\text{-}(EO)_l\text{-}R^{2a} \qquad (A1)$$

wherein, $R^{1a}$ represents a linear or branched, alkyl or alkenyl group having 10 to 16 carbon atoms; EO represents an ethyleneoxy group; l represents an average mole number of ethyleneoxy groups added, ranging from 3 to 40; and $R^{2a}$ represents a hydrogen atom or a methyl group, (A2): a polyoxyethylene fatty acid ester,
wherein a fatty acid group has 8 to 16 carbon atoms; and an average number of moles of ethylene oxide added per mole of fatty acid is 5 to 40, (A3): a polyoxyethylene sorbitan fatty acid ester,
wherein a fatty acid group has 8 to 16 carbon atoms; and an average number of moles of ethylene oxide added per mole of fatty acid is 5 to 40, (A4): a (poly)glycerol fatty acid ester,
wherein a fatty acid group has 8 to 16 carbon atoms; and an average condensation degree of glycerol is 1 to 3, and (A5): an alkyl saccharide represented by the formula (A5):

$$R^{3a}\text{—}O\text{-}(G)_p \qquad (A5)$$

wherein $R^{3a}$ represents an alkyl group having 8 to 16 carbon atoms; G represents a reducing sugar group having 5 to 6 carbon atoms; and p represents a number of 1 to 10;

(B1): a polyoxyalkylene alkyl ether represented by the formula (B1):

$$R^{1b}O\text{—}[(PO)_m/(EO)_n]\text{—}R^{2b} \qquad (B1)$$

wherein, $R^{1b}$ represents a linear or branched, alkyl or alkenyl group having 6 to 12 carbon atoms; PO represents a propyleneoxy group; EO represents an ethyleneoxy group; m represents an average mole number of propyleneoxy groups added, ranging from 2 to 20; n represents an average mole number of ethyleneoxy groups added, which is 0; and $R^{2b}$ represents a hydrogen atom or a methyl group; wherein "/" means that PO and EO groups may be arranged at random or in blocks, and (B2): an aliphatic alcohol represented by the formula (B2):

$$R^{3b}\text{—}OH \qquad (B2)$$

wherein $R^{3b}$ represents a linear or branched, alkyl group having 8 to 10 carbon atoms, and wherein a weight ratio of compounds (A) to (B), (A)/(B), is 0.5 to 8.

2. The method for producing an agricultural product according to claim 1, provided that when B is (B1) then A is (A1), and when B is (B2) then A is (A2) or (A4).

3. The method for producing an agricultural product according to claim 1, wherein the total weight of compounds (A) and (B)/the weight of the agricultural chemical ingredient is from 0.1 to 100.

4. The method for producing an agricultural product according to claim 1, wherein the agricultural chemical composition further comprises water and/or an organic solvent.

5. The method for producing an agricultural product according to claim 1, comprising contacting the agricultural chemical composition with a part of a plant where a water contact angle is 50 to 180 degrees.

6. The method for producing an agricultural product according to claim 1, wherein the total content of compounds (A) and (B) in an agricultural chemical preparation for spray is 30 to 50000 ppm.

7. The method for producing an agricultural product according to claim 1, comprising spraying the agricultural chemical preparation for spray in an amount of 1 to 500 L/10a.

8. A method for producing an agricultural product, comprising a step of applying an agricultural chemical composition comprising (A) at least one compound selected from the group consisting of the following (A1) to (A5); (B) at least one compound selected from the group consisting of the following (B1) and (B2); and an agricultural chemical ingredient selected from the group consisting of active ingredients in bactericides, pesticides, miticides, herbicides and plant growth regulators to a subject sensitive to the agricultural chemical ingredient:

(A1): a polyoxyethylene alkyl ether represented by the formula (A1):

$$R^{1a}O\text{-}(EO)_l\text{-}R^{2a} \qquad (A1)$$

wherein, $R^{1a}$ represents a linear or branched, alkyl or alkenyl group having 10 to 14 carbon atoms; EO represents an ethyleneoxy group; l represents an average mole number of ethyleneoxy groups added, ranging from 3 to 40; and $R^{2a}$ represents a hydrogen atom or a methyl group, (A2): a polyoxyethylene fatty acid ester,
wherein a fatty acid group has 10 to 14 carbon atoms; and an average number of moles of ethylene oxide added per mole of fatty acid is 6 to 12, (A3): a polyoxyethylene sorbitan fatty acid ester,
wherein a fatty acid group has 10 to 14 carbon atoms; and an average number of moles of ethylene oxide added per mole of fatty acid is 6 to 20, (A4): a (poly)glycerol fatty acid ester,
wherein a fatty acid group has 8 to 12 carbon atoms; and an average condensation degree of glycerol is 1 to 2, and (A5): an alkyl saccharide represented by the formula (A5):

$$R^{3a}\text{—}O\text{-}(G)_p \qquad (A5)$$

wherein $R^{3a}$ represents an alkyl group having 10 to 12 carbon atoms; G represents a reducing sugar group having 5 to 6 carbon atoms; and p represents a number of 1 to 5;

(B1): a polyoxyalkylene alkyl ether represented by the formula (B1):

$$R^{1b}O\text{—}[(PO)_m/(EO)_n]\text{—}R^{2b} \qquad (B1)$$

wherein, $R^{1b}$ represents a linear or branched, alkyl or alkenyl group having 6 to 12 carbon atoms; PO represents a propyleneoxy group; EO represents an ethyleneoxy group; m represents an average mole number of propyleneoxy groups added, ranging from 2 to 10; n represents an average mole number of ethyleneoxy groups added, which is 0; and $R^{2b}$ represents a hydrogen atom or a methyl group; wherein "/" means that PO and EO groups may be arranged at random or in blocks, and (B2): an aliphatic alcohol represented by the formula (B2):

$$R^{3b}\text{—OH} \tag{B2}$$

wherein $R^{3b}$ represents a linear or branched, alkyl group having 8 to 10 carbon atoms, and wherein a weight ratio of compounds (A) to (B), (A)/(B), is 0.5 to 8.

9. The method for producing an agricultural product according to claim 8, provided that when B is (B1) then A is (A1), and when B is (B2) then A is (A2) or (A4).

10. The method for producing an agricultural product according to claim 8, wherein the agricultural chemical composition further comprises water and/or an organic solvent.

11. The method for producing an agricultural product according to claim 8, comprising contacting the agricultural chemical composition with a part of a plant where a water contact angle is 50 to 180 degrees.

12. The method for producing an agricultural product according to claim 8, comprising spraying the agricultural chemical preparation for spray in an amount of 1 to 500 L/10a.

* * * * *